(12) United States Patent
Ho et al.

(10) Patent No.: US 11,896,843 B2
(45) Date of Patent: Feb. 13, 2024

(54) PHOTODYNAMIC THERAPY DEVICES, SYSTEMS AND METHODS

(71) Applicant: NATIONAL UNIVERSITY OF SINGAPORE, Singapore (SG)

(72) Inventors: John Ho, Singapore (SG); Yong Zhang, Singapore (SG); Akshaya Bansal, Singapore (SG); Fengyuan Yang, Singapore (SG); Xi Tian, Singapore (SG)

(73) Assignee: NATIONAL UNIVERSITY OF SINGAPORE, Singapore (SG)

(*) Notice: Subject to any disclaimer, the term of this patent is extended or adjusted under 35 U.S.C. 154(b) by 0 days.

(21) Appl. No.: 16/964,829

(22) PCT Filed: Jan. 22, 2019

(86) PCT No.: PCT/SG2019/050037
§ 371 (c)(1),
(2) Date: Jul. 24, 2020

(87) PCT Pub. No.: WO2019/147185
PCT Pub. Date: Aug. 1, 2019

(65) Prior Publication Data
US 2021/0060350 A1 Mar. 4, 2021

(30) Foreign Application Priority Data
Jan. 24, 2018 (SG) .............. 10201800633S

(51) Int. Cl.
*A61N 5/06* (2006.01)
(52) U.S. Cl.
CPC ........... *A61N 5/062* (2013.01); *A61N 5/0601* (2013.01); *A61N 2005/0612* (2013.01); *A61N 2005/0626* (2013.01)

(58) Field of Classification Search
CPC .............. A61N 5/062; A61N 5/0601; A61N 2005/0612; A61N 2005/0626; H02J 50/20
See application file for complete search history.

(56) References Cited

U.S. PATENT DOCUMENTS 9,669,231 B1 * 6/2017 Clark .................. A61N 5/025
2010/0305666 A1 12/2010 Lou et al.
(Continued)

FOREIGN PATENT DOCUMENTS

CN 101375790 A 3/2009
WO WO-2008067455 A2 * 6/2008 .......... A61N 5/0601
(Continued)

OTHER PUBLICATIONS

"An Implantable MOSFET Dosimeter for the Measurement of Radiation Dose in Tissue During Cancer Therapy." Beyer et al. IEEE Sensors Journal, vol. 8 No. 1, Jan. 2008. (Year: 2008).*
T. Lu, Z. Zhao, S. Ji, H. Yu and L. Yuan, "Active Clamping Circuit With Status Feedback for Series-Connected HV-IGBTs," in IEEE Transactions on Industry Applications, vol. 50, No. 5, pp. 3579-3590, Sep.-Oct. 2014, doi: 10.1109/TIA.2014.2308356. (Year: 2014).*
(Continued)

*Primary Examiner* — Gary Jackson
*Assistant Examiner* — Ranjani Mari Sundaresan
(74) *Attorney, Agent, or Firm* — Harness, Dickey & Pierce, P.L.C.

(57) ABSTRACT

Wirelessly powered photodynamic therapy devices are disclosed and systems and methods using such devices are also disclosed. In an embodiment, a photodynamic therapy system comprises: an implantable illumination device comprising a light source configured to emit light having a spectrum which overlaps with an absorption peak of an absorption target and a receiver antenna coupled to the light source and configured to extract power from a radiofrequency power signal incident on the implantable illumination device; and a transmitter comprising an antenna, a powering module configured to generate a drive signal which causes the antenna to generate the radiofrequency power signal, and a (Continued)

dosimetry module coupled to the antenna and configured to detect a radiofrequency signal backscattered from the implantable illumination device and determine an indication of the power extracted by the implantable illumination device from the radiofrequency signal backscattered from the implantable illumination device.

8 Claims, 20 Drawing Sheets

(56) References Cited

U.S. PATENT DOCUMENTS

| | | | |
|---|---|---|---|
| 2014/0128943 A1 | | 5/2014 | Rogers et al. |
| 2017/0224248 A1 | | 8/2017 | Zou et al. |

FOREIGN PATENT DOCUMENTS

| | | | | |
|---|---|---|---|---|
| WO | 2013025632 A1 | | 2/2013 | |
| WO | WO-2014176432 A1 | * | 10/2014 | ......... A61N 1/37217 |
| WO | 2017004531 A1 | | 1/2017 | |
| WO | WO-2017004576 A1 | * | 1/2017 | ......... A61B 5/14503 |
| WO | WO-2017176908 A1 | * | 10/2017 | ............. H02J 7/025 |
| WO | WO-2018009905 A2 | * | 1/2018 | ........... A61N 1/3605 |

OTHER PUBLICATIONS

Bansal A. et al., "In vivo wireless photonic photodynamic therapy", PNAS, Feb. 13, 2018, vol. 115, No. 7, pp. 1469-1474 [Retrieved on Mar. 21, 2019].

Montgomery K. L. et al., "Wirelessly powered, fully internal optogenetics for brain, spinal and peripheral circuits in mice", Nature Methods, Aug. 17, 2015, vol. 12, pp. 969-974 [Retrieved on Mar. 21, 2019].

Park S. et al., "Soft, stretchable, fully implantable miniaturized optoelectronic systems for wireless optogenetics", Nat Biotechnol., Dec. 1, 2015, vol. 33, No. 12, pp. 1280-1286 (NIH Public Access Author Manuscript in PMC) [Retrieved on Mar. 21, 2019 from <https://www.ncbi.nlm.nih.gov/pmc/articles/PMC4880021/>].

Tian X. et al., "Control of wireless power transfer to a bioelectronic device by harmonic feedback", AIP Advances, Sep. 12, 2018, vol. 8, No. 095308, pp. 1-8 [Retrieved on Mar. 21, 2019].

Lucky S. S. et al., "Nanoparticles in Photodynamic Therapy", Chemical Reviews, Jan. 20, 2015, vol. 115, No. 4, pp. 1990-2042 [Retrieved on Mar. 21, 2019].

International Search Report and Written Opinion of the International Searching Authority issued in PCT/SG2019/050037, dated Apr. 10, 2019; ISA/SG.

First Office Action for Chinese Application No. 201980010202.5 dated Nov. 23, 2021 with English language translation; 25 pages.

* cited by examiner

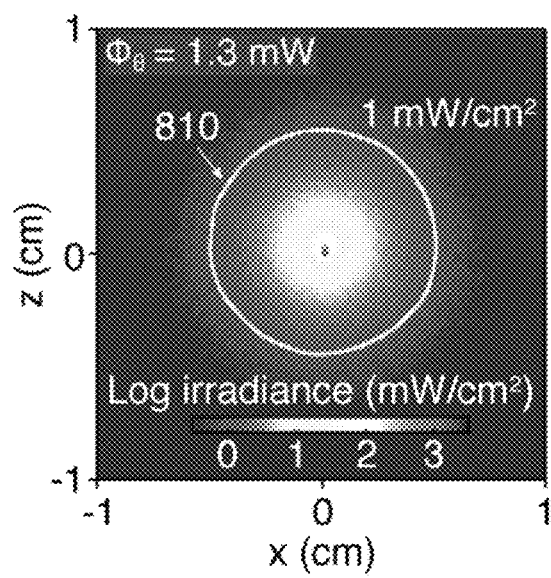 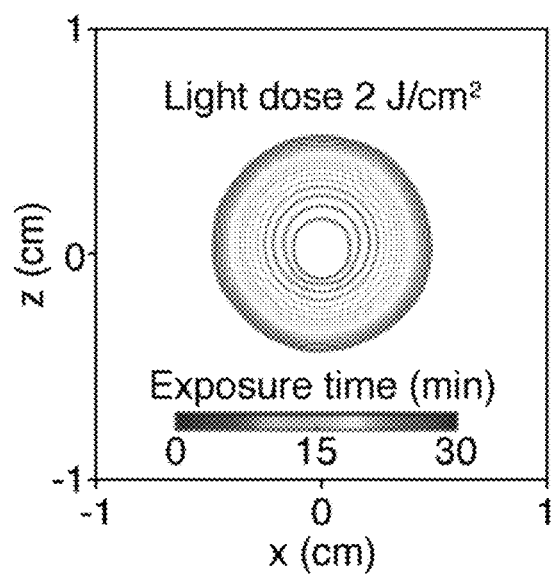
Figure 8a        Figure 8b
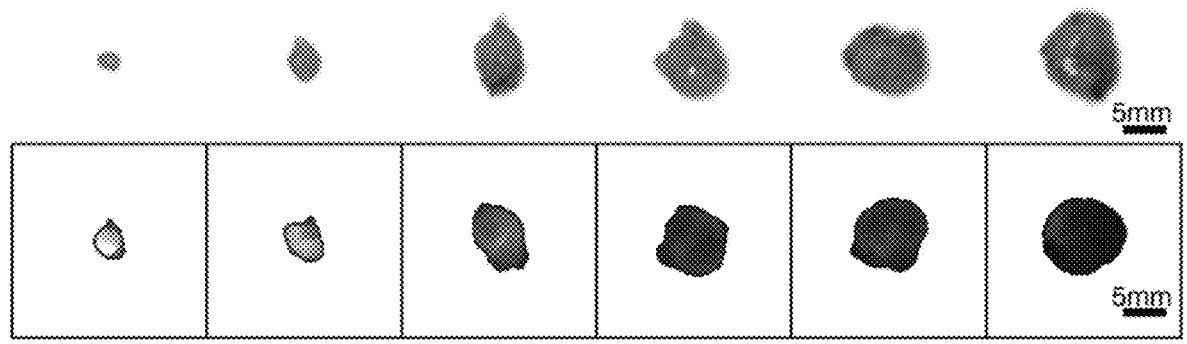
Figure 9

PHOTODYNAMIC THERAPY DEVICES, SYSTEMS AND METHODS

CROSS REFERENCE TO RELATED APPLICATIONS

This Application is a U.S. National Application under 35 U.S.C. 371 of International Application No. PCT/SG2019/050037filed on Jan. 22, 2019, which claims the benefit of priority from Singapore Patent Application No. 10201800633S filed on Jan. 24, 2018. The entire disclosures of all of the above applications are incorporated herein by reference.

TECHNICAL FIELD

The present disclosure relates to photodynamic therapy and in particular to photodynamic therapy devices, systems and methods in which power is wirelessly transmitted to an implantable illumination device.

BACKGROUND

Advances in understanding and engineering light-tissue interactions have enabled a class of targeted therapies with unmatched spatiotemporal resolution. Photodynamic therapy (PDT) is a clinical example in which light-sensitive drugs known as photosensitizers are selectively activated by light, producing reactive oxygen species (ROS) which can be used to kill malignant cells. Other emerging treatments include photothermal therapy and photobiomodulation. Clinical application of PDT, however, has been hindered by the low penetration of light through biological tissue, which limits the therapeutic depth to less than a centimeter, even at near-infrared wavelengths. Currently, light delivery into deeper tissue regions relies on optical fibers inserted through surgery or endoscopy, but their incompatibility with long-term implantation allows only a single light dose to be delivered. This limitation in light delivery precludes the use of PDT for long-term therapy in order to suppress tumor recurrence or to tailor the dose to the tumor response.

SUMMARY OF THE INVENTION

According to a first aspect of the present disclosure a photodynamic therapy system comprises: an implantable illumination device comprising a light source configured to emit light having a spectrum which overlaps with an absorption peak of an absorption target and a receiver antenna coupled to the light source and configured to extract power from a radiofrequency power signal incident on the implantable illumination device; and a transmitter comprising an antenna, a powering module configured to generate a drive signal which causes the antenna to generate the radiofrequency power signal, and a dosimetry module coupled to the antenna and configured to detect a radiofrequency signal backscattered from the implantable illumination device and determine an indication of the power extracted by the implantable illumination device from the radiofrequency signal backscattered from the implantable illumination device.

In an embodiment, the light source comprises a first light emitting device configured to emit light having a first wavelength and a second light emitting device configured to emit light having a second wavelength different from the first wavelength.

In an embodiment, the implantable illumination device comprises a printed circuit board and a plurality of electronic components mounted on the printed circuit board and wherein the receiver antenna comprises a helical coil having a plurality of turns around the printed circuit board.

In an embodiment, the implantable illumination device comprises a planar substrate and wherein the light source comprises a plurality of light emitting devices arranged on the planar substrate. The receiver antenna may comprise a conductive loop formed on the planar substrate. The planar substrate may be formed from a flexible material.

In an embodiment the receiver antenna is configured to provide a resonance for a range of frequencies including the radiofrequency power signal.

In an embodiment, the implantable illumination device is encapsulated in an encapsulation material.

In an embodiment, wherein the implantable illumination device comprises at least one flap formed from the encapsulation material.

In an embodiment, the implantable illumination device comprises a regulator circuit configured to reduce variations emitted light intensity from the light source due to changes in power extracted by the implantable illumination device.

In an embodiment the regulator circuit comprises a clamp circuit. In an embodiment, the clamp circuit comprises a zener diode.

In an embodiment, the radiofrequency signal backscattered from the implantable illumination device is a harmonic of the radiofrequency power signal.

In an embodiment, the transmitter is configured to control the radiofrequency power control signal based on the indication of the power extracted by the implantable illumination device to control an illumination dose provided by the implantable illumination device.

In an embodiment, the transmitter is configured to provide an indication of the indication of the power extracted to a user.

in an embodiment, the radio frequency power signal has a frequency in the range 1 to 5 GHz.

In an embodiment the transmitter further comprises a controller configured to modify the drive signal to spatially focus the radiofrequency power signal on the implantable illumination device.

In an embodiment, the transmitter operates in either the electromagnetic near-field (close range, <1 cm distance) or midfield (deep in tissue, >1 cm) ranges and spatially shapes the radio-frequency field in order to focus energy on the device.

In some embodiments, the absorption target is a photosensitizer. In some embodiments, the absorption target is a light transducer selected to emit light having a spectrum that overlaps with an absorption peak of a photosensitizer.

According to a second aspect of the present disclosure, an implantable illumination device comprises a light source configured to emit light having a spectrum which overlaps with an absorption peak of an absorption target and a receiver antenna coupled to the light source and configured to extract power from a radiofrequency power signal incident on the implantable illumination device.

According to a third aspect of the present disclosure transmitter for a photodynamic therapy system, comprises: an antenna, a powering module configured to generate a drive signal which causes the antenna to generate a radiofrequency power signal to wirelessly provide power to an implantable illumination device, and a dosimetry module coupled to the antenna and configured to detect a radiofrequency signal backscattered from the implantable illumination device and determine an indication of the power extracted by the implantable illumination device from the radio frequency signal backscattered from the implantable illumination device.

According to a fourth aspect of the present disclosure a method of treating a tumor in a patient comprises implanting an implantable illumination device proximate to or within the tumor; administering a photosensitizer to the patient; and transmitting a radiofrequency power signal to the implantable illumination device.

In an embodiment the method further comprises receiving a backscattered radiofrequency signal from the implantable illumination device and determining a light dose applied to the tumor from the received backscattered signal.

In an embodiment the method further comprises adjusting the radiofrequency power signal to control the light dose applied to the tumor.

In an embodiment, adjusting the radiofrequency power signal comprises adjusting a polarization, or focus location of the radiofrequency power signal and/or changing a location or orientation of a transmitter of the radiofrequency power signal.

In an embodiment, the method further comprises administering a light transducer material to the patient, the light transducer material being selected to emit light having a spectrum that overlaps with an absorption peak of the photosensitizer.

BRIEF DESCRIPTION OF THE DRAWINGS

In the following, embodiments of the present invention will be described as non-limiting examples with reference to the accompanying drawings in which:

FIGS. 8a and 8b shows the results of a numerical simulation of optical irradiance around a device embedded in homogenous tumor-like tissue;

FIG. 9 shows images of the penetration of light emitted by an implantable illumination device through tumors of different volume;

DETAILED DESCRIPTION

The present disclosure relates to a wireless photonic approach to photodynamic therapy (PDT) that enables on-demand light activation of photosensitizers deep in the body. A system comprising an implantable photonic device and a wireless powering system delivers therapeutic doses of light into tissues inaccessible by direct illumination. The miniaturized (30 mg, 15 mm³) dimensions of the device allows its direct implantation at the target site, where a specialized radio-frequency system wirelessly powers the device and monitors the light dosing rate.

Figure 1:
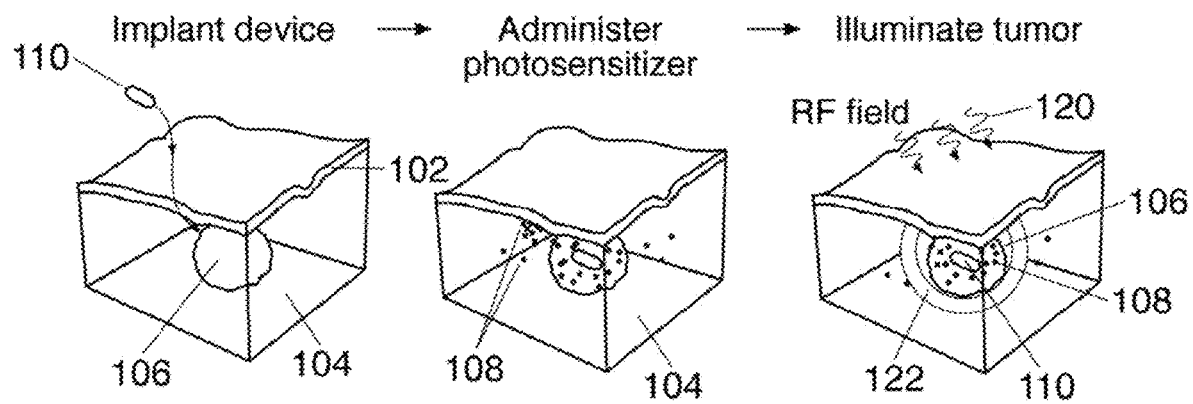
FIG. 1 shows a schematic of a photodynamic therapy method.

FIG. 1 shows a schematic of the PDT method for treating a lesion. First, the implantable illumination device 110 is inserted through the skin 102 of a patient 104 near the target lesion 106. Because of its small dimensions, the implantable illumination device 110 is compatible with minimally invasive implantation during standard clinical procedures such as incisional biopsy or during surgical tumor resection to combat tumor recurrence. Second, a photosensitizer 108 is administered to the patient 104. The photosensitizer 108 is by itself harmless. Finally, the implantable illumination device 110 is wirelessly powered, with a radiofrequency signal 120, which causes the implantable illumination device 110 to illuminate the target lesion 106 with light 122 having a wavelength or spectrum of wavelengths selected to activate the photosensitizer 108. The illumination results in the localized production of cytotoxic reactive oxygen species (ROS) from the photosensitizer 108 that directly kill malignant cells, damage the tumor microvasculature, and/or stimulate the host immune response. By spatially and temporally controlling the light dose, the therapy can be tailored for maximum efficacy and minimum side effects.

In some embodiments, as is described in more detail below with reference to FIGS. 35 and 36, a light transducer material, such as up-conversion nanoparticles (UCNPs) is administered to the patient in addition to the photosensitizer. The light transducer material is selected to emit light which activates the photosensitizer in response to absorbing light of a different wavelength. The use of such a light transducer material allows treatment of larger tumors since wavelength of light emitted by the implantable illumination device can be selected as, for example near infra-red (NIR) which has a greater penetration depth than light in the visible or ultraviolet range of the spectrum.

Figure 2:
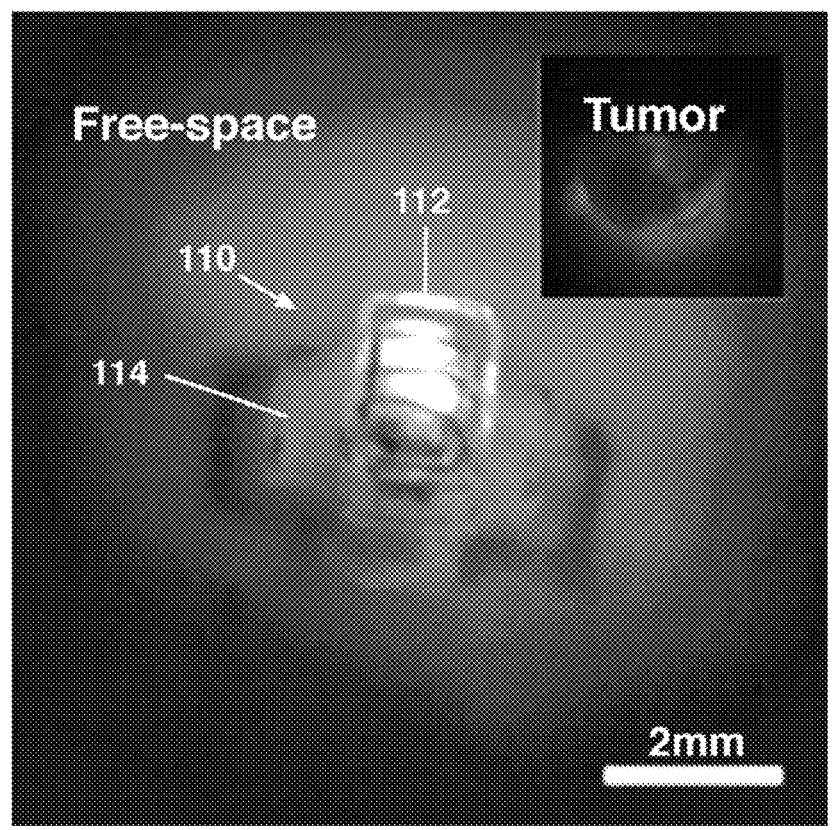
FIG. 2 shows an image of the implantable illumination device.

FIG. 2 shows an image of the implantable illumination device. The inset shows the device illuminating an explanted tumor. As shown in FIG. 2, the implantable illumination device 110 is encapsulated with an encapsulation material 112 which is optically transparent such as medical-grade silicone. Flaps 114 are formed from the encapsulation material to control the orientation of the implantable illumination device 110 and to facilitate fixation using sutures. As shown in FIG. 2, the largest diameter of the implantable illumination device 110 is around 3 mm.

Figure 3:
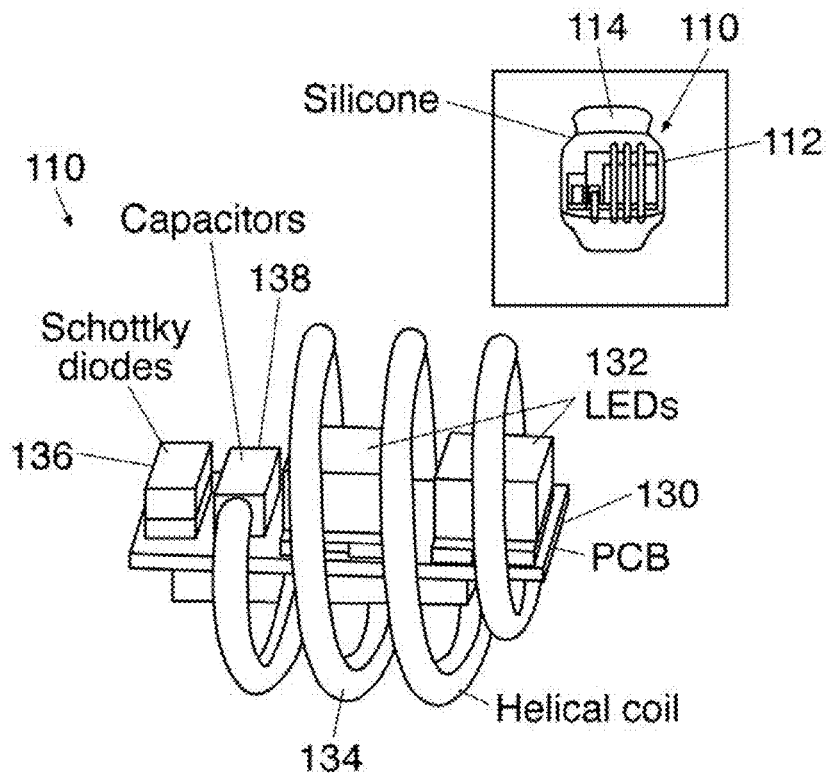
FIG. 3 shows a schematic of the implantable illumination device.

FIG. 3 shows a schematic of the implantable illumination device. As shown in FIG. 3, the implantable illumination device 110 comprises a custom two-sided printed circuit board (PCB) 130. Two surface mount LEDs 132 are mounted on the PCB 130. As will be described in more detail below, the LEDs 132 are selected to provide an optical emission spectrum to activate the photosensitizer. In this example, the LEDs 132 provide red (660 nm) and violet (400 nm) emissions respectively. The implantable illumination device 110 further comprises a three-turn helical coil 134 for receiving radio-frequency energy, and a rectifier for alternating current to direct current conversion formed from surface mount capacitors 138 and radio-frequency Schottky diodes 136. The helical coil 134 is formed from enameled wire. The electrical components are mounted on the PCB 130 using lead-free soldering materials. The helical coil is arranged to maximize the fraction of the device volume that it occupies and therefore maximize the collected power by the coil.

As shown in the inset of FIG. 3, the implantable illumination device 110 is encapsulated with an encapsulation material 112 which may comprise Polydimethylsiloxane (PDMS) and a silicone elastomer. Flaps 114 are formed from the encapsulation material.

Figure 4:
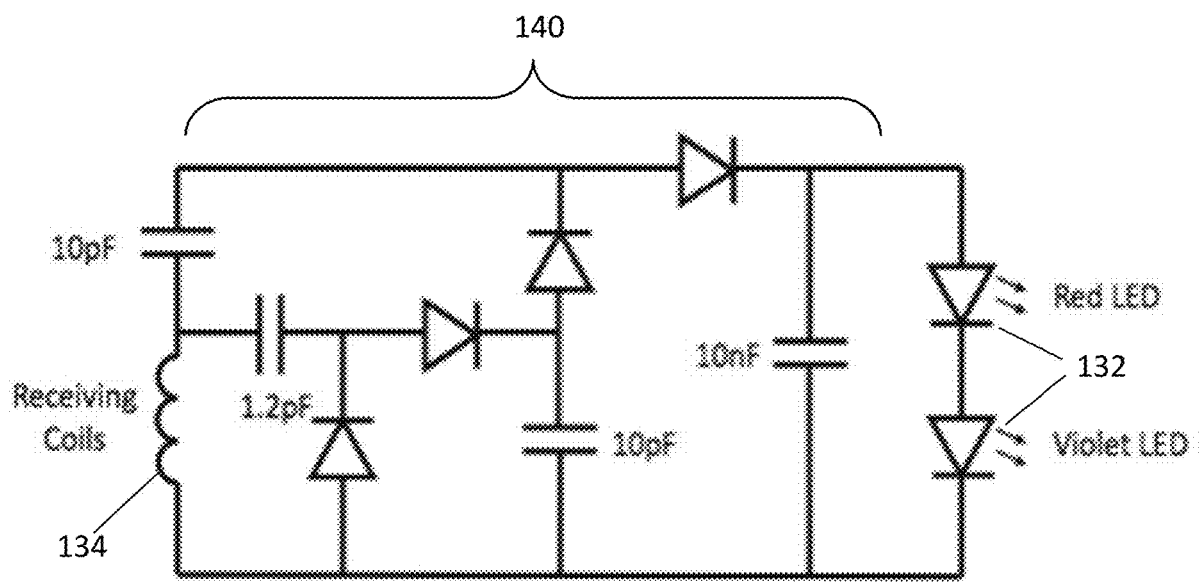
FIG. 4 shows a circuit diagram of the implantable illumination device.

FIG. 4 shows a circuit diagram of the implantable illumination device. As shown in FIG. 4, the LEDs 132 are connected in series. A rectifier 140 formed from the capacitors and diodes connects the helical coil 134 to the LEDs 132. The rectifier 140 acts to convert the alternating current signal received by the helical coil 134 to a direct current which powers the LEDs 132.

The dimensions of the helical coil 134 are selected such that the combined circuit exhibits a resonance in the operating frequency range, which also enhances power collection.

Figure 5:
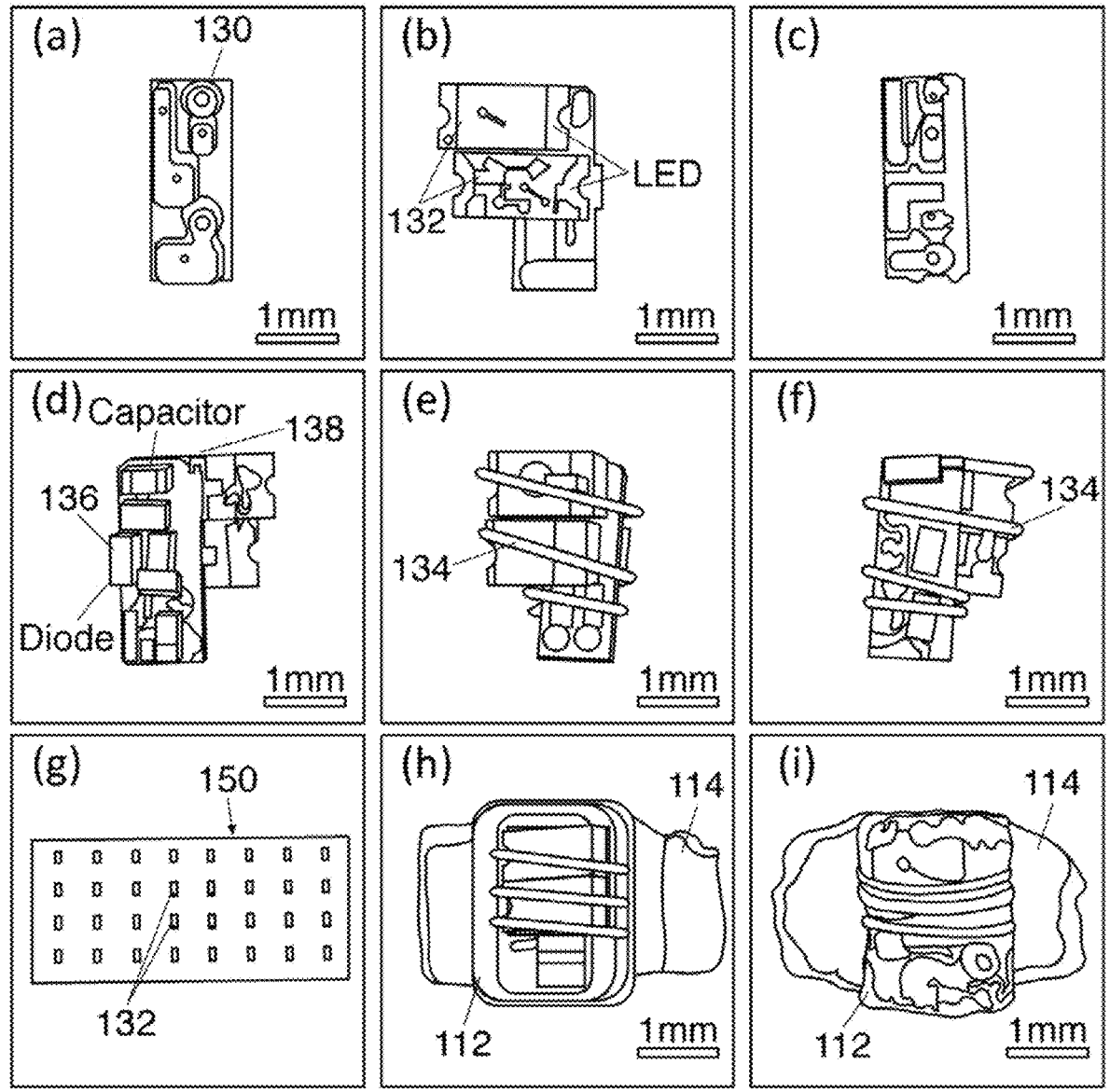
FIGS. 5a to 5i show the assembly of the implantable illumination device.

FIGS. 5a to 5i show the assembly of the implantable illumination device. As shown in FIG. 5a, the PCB 130 was laser cut to the exact size. Then, as shown in FIG. 5b, the LEDs 132 were mounted using micro-soldering under a microscope. On the reverse side shown in FIG. 5c, the diodes and capacitors were mounted as shown in FIG. 5d. As shown in FIGS. 5e and 5f, the helical coil 134 was formed around the device by wrapping enameled wire three times around the assembled PCB and soldering the two ends on designed pads.

As shown in FIG. 5g, multiple devices 110 were encapsulated in a 3-D printed mold 150 by pouring PDMS, degassing in a vacuum chamber for one hour, and curing in a forced convection oven. As shown in FIGS. 5h and 5i, the encapsulated devices were removed from the mold and coated with a thin layer of rapid curing, biocompatible silicone 112 to enhance electrical isolation and surface smoothness. Encapsulation materials should be transparent to radio-frequency fields and light, including but not limited to silicone, glass, ceramics, and epoxies. As described above, flaps 114 are formed from the encapsulation material or the silicone coating.

Figure 6:
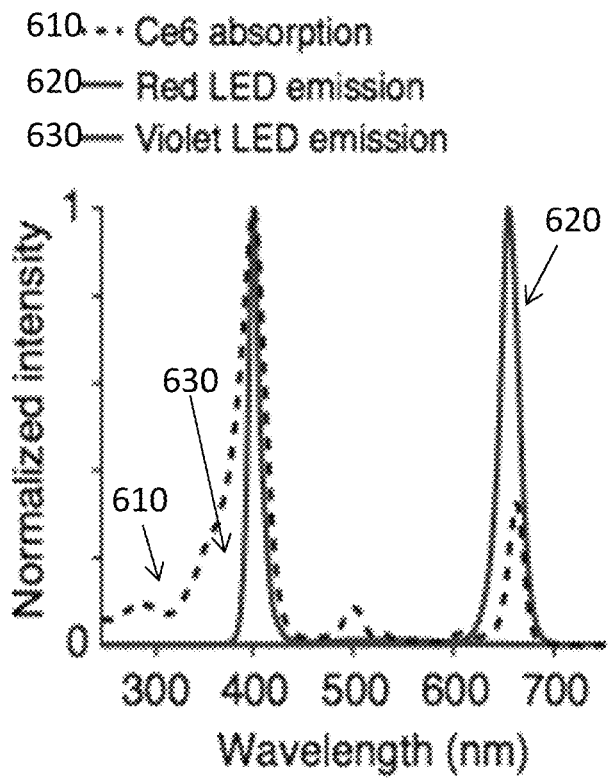
FIG. 6 is a graph showing the emission spectrum of LEDs in an implantable illumination device and the absorption spectrum of the photosensitizer.

FIG. 6 is a graph showing the emission spectrum of LEDs in an implantable illumination device and the absorption spectrum of the photosensitizer. The exemplary implantable illumination device described herein is configured to be used with the photosensitizer Chlorin e6 (Ce6). As shown in FIG. 6, the photosensitizer emission spectrum 610 has peaks at around 400 nm and 660 nm. Thus the violet LED having an emission spectrum with a peak at around 400 nm and the red LED having an emission spectrum with a peak at around 660 nm are selected so that the peaks of the emission spectrum from the two LEDs matches the peaks of the absorption spectrum of the photosensitizer. Ce6 is a clinically approved photosensitizer widely used for cancer treatment. It will be appreciated that the general configuration can be used with any photosensitizer, with the emission spectrum of the LEDs selected to overlap with the activation spectrum of the photosensitizer.

Figure 7A:
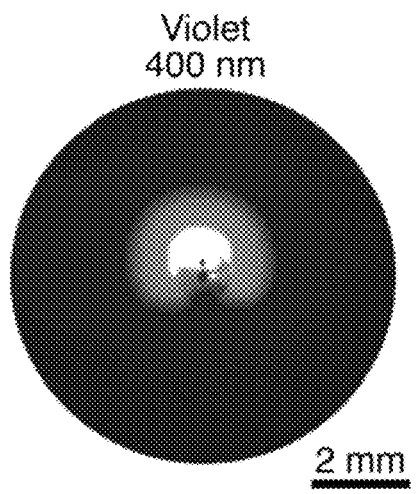
FIGS. 7a and 7b are images of the light distribution of violet light, and red light, respectively around the implantable illumination device on a synthetic tissue slab.
Figure 7B:
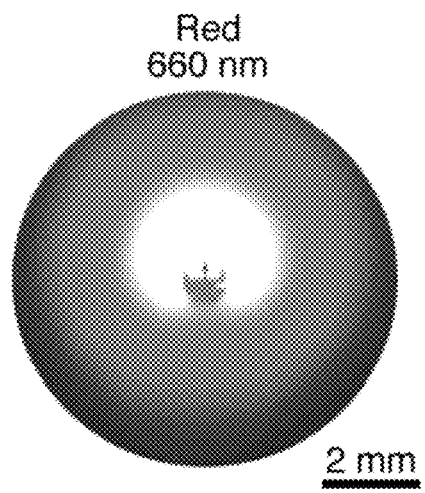

FIGS. 7a and 7b are images of the light distribution of violet light, and red light, respectively around the implantable illumination device on a synthetic tissue slab. As shown in FIGS. 7a and 7b, the irradiance contours approximate a sphere with center offset in the direction of emission at both wavelengths owing to light scattering. The direction of emission in FIGS. 7a and 7b is upwards towards the top of the page. The emission is directional, indicating control of the orientation of the LEDs is important, although optical scattering limits the spatial selectivity of the light delivery.

FIGS. 8a and 8b shows the results of a numerical simulation of optical irradiance around a device embedded in homogenous tumor-like tissue. FIG. 8a shows $\phi_e$ which is the emitted radiant power, or equivalently the light dosing rate. The solid white contour 810 shows a 1 mW/cm$^2$ irradiance contour. The simulations estimate that at a total radiant power of 1.3 mW, the irradiance reaches 1 mW/cm$^2$ at a radius of 4 mm for red and 1.2 mm for violet light in the direction of maximum intensity.

FIG. 8b shows light dose contours of a 2 J/cm² does for exposure times of 1 to 30 minutes. As shown in FIG. 8b, At the radius mentioned above (4 mm for red and 1.2 mm for violet light in the direction of maximum intensity) the resulting optical exposure of 2 J/cm² is reached over a period of 30 min, which is sufficient to activate most photosensitizers.

FIG. 9 shows images of the penetration of light emitted by an implantable illumination device through tumors of different volume. The upper images in FIG. 9 show the tumors which have increasing diameters from left to right from approximately 2 mm to approximately 10 mm. The lower images show the illuminated tumors. The device used to provide the illumination in the images in FIG. 9 has a radiant power of 1.3 mW. As illustrated in FIG. 9, the device emits light when wirelessly powered in a radio-frequency field with sufficient radiant power to fully illuminate a tumor volume about 5 mm in diameter (the third image from the left hand side).

Figure 10:
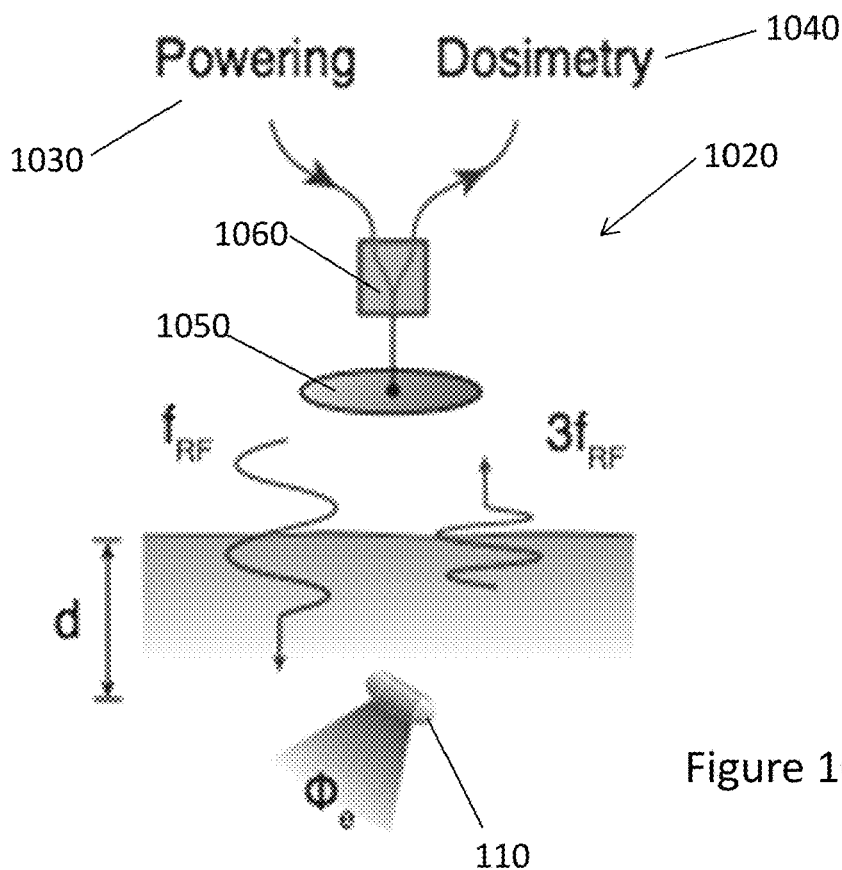
FIG. 10 shows a schematic of a system comprising the implantable illumination device and a transmitter for generating a radiofrequency power signal.

FIG. 10 shows a schematic of a system comprising the implantable illumination device and a transmitter for generating a radiofrequency power signal. The transmitter 1020 comprises a powering module 1030 and a dosimetry module. The transmitter 1020 also comprises an antenna 1050 which is coupled to the powering module 1030 and the dosimetry module 1040 by a coupler 1060.

In operation, the powering module 1030 drives antenna with a radio-frequency signal having a frequency $f_{RF}$ between 1 to 5 GHz. Transmitters were designed for operation both in the electromagnetic near-field (close range, <1 cm distance) and midfield (deep in tissue, >1 cm) ranges. As shown in FIG. 10, the transmitter 1020 wirelessly powers the implantable illumination device 110 which is at a depth of d with a signal having a frequency $f_{RF}$. The backscattered third harmonic signal having a frequency $3f_{RF}$ is measured to establish the emitted radiant power $\phi_e$ of the implantable illumination device 110.

The dosimetry module 1040 controls the light dose delivered to the target region. The control by the dosimetry module 1040 is based on the measurement of harmonic signals including the third harmonic signal having a frequency $3f_{RF}$ backscattered during wireless powering. Wireless powering for a prescribed light doing rate was established in two steps: (1) while holding the transmit power constant, the transmitter position was adjusted until the measured harmonic backscatter was maximized (compensating for potential misalignment between the transmitter and receiver); (2) while holding the transmitter position constant, the transmit power was tuned such that the light emission was set to the desired level using the dosimetry module 1040.

The antenna 1050 may allow spatial shaping of the radiofrequency power signal. For example, the antenna 1050 may comprise a plurality of excitation ports and the transmitter 1020 may comprise a controller configured to adjust a phase and/or amplitude delivered to the excitation ports to allow spatial shaping of the electromagnetic field of the radiofrequency power signal. Examples of such transmitters are provided in US Patent Application Publication US2016/0339256.

Figure 11:
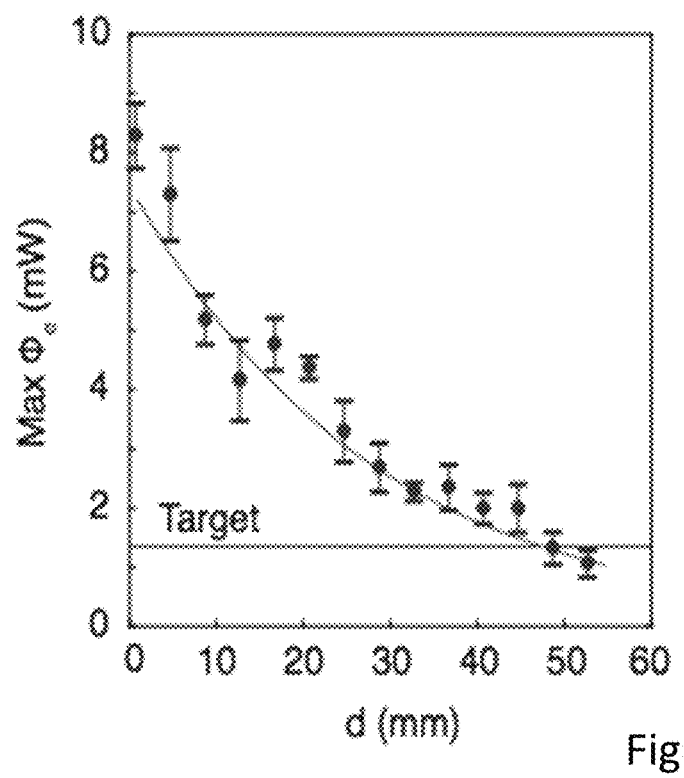
FIG. 11 is a graph showing the maximum radiant power as a function of depth of the device.

FIG. 11 is a graph showing the maximum radiant power as a function of depth of the device. The graph shown in FIG. 11 was generated using data for a device in tissue simulating water. The graph shows the maximum radiant power $\phi_e$ when the device was powered in a midfield configuration with an output power $P_{RF}$ from the transmitter of 2W. FIG. 11 shows that in the midfield configuration, the maximum radiant power that can be delivered by the device exceeds 1 mW at a 4 cm depth in water at a transmit power of 2 W. The target power of 1.3 mW is reached for depths of around 48 mm.

The sensitivity of light delivery to variations in wireless powering can be further reduced by incorporating a clamping circuit to limit light emission beyond the target rate. This is illustrated in FIG. 12.

Figure 12:
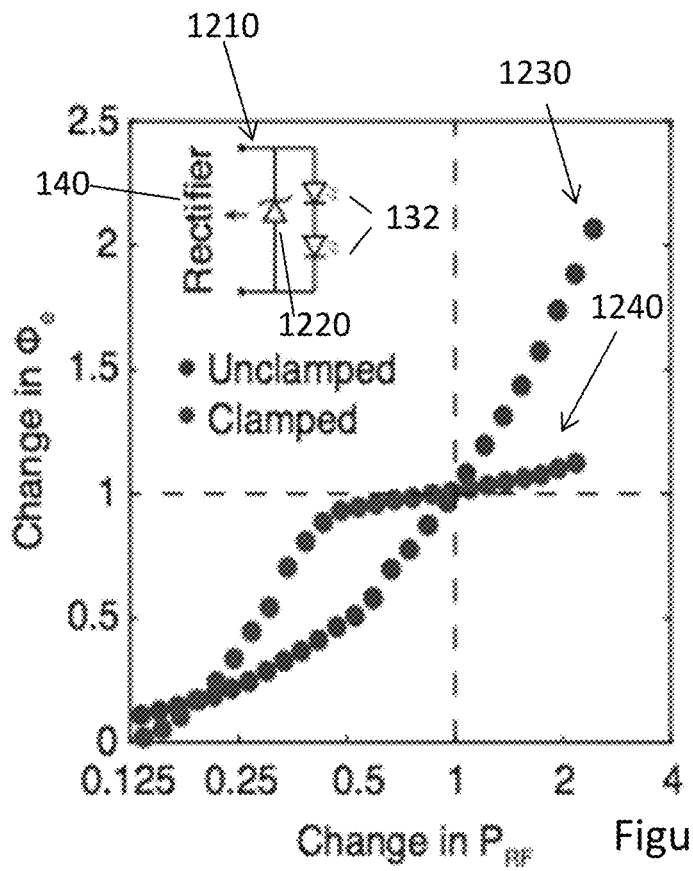
FIG. 12 shows the change in emitted radiant power as a function of the output power of the transmitter for a device with and without a clamping circuit.

FIG. 12 shows the change in emitted radiant power as a function of the output power of the transmitter for a device with and without a clamping circuit. The inset of FIG. 12 shows an example of the clamping circuit.

As shown in the inset of FIG. 12, the clamping circuit 1210 comprises a zener diode 1220 connected in parallel with the two LEDs and the output of the rectifier 140. FIG. 12 shows data points for an unclamped device 1230 (an implantable illumination device without a clamping circuit) and for a clamped device 1240 (an implantable illumination device with a clamping circuit—as shown in the inset of FIG. 12). As illustrated in FIG. 12, across a twofold increase or decrease in power level around the operating point (radiant power, 1.3 mW), the clamping circuit reduces the variation in light output from 70% to less than 10%.

Figure 13:
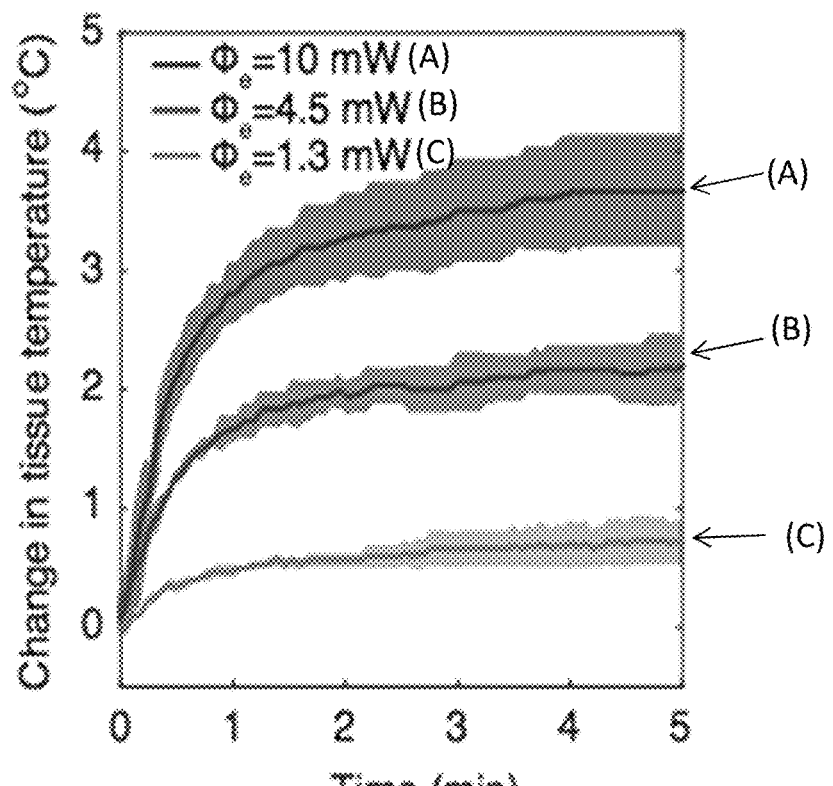
FIG. 13 is a graph showing heating of tumor tissue under light exposure.

FIG. 13 is a graph showing heating of tumor tissue under light exposure. FIG. 13 shows the change in tissue temperature against time for different exposure powers. The curves in FIG. 13 show powers of $\phi_e$=10 mW (A); $\phi_e$=4.5 mW (B); and $\phi_e$=1.3 mW (C). The lines in the graph show the mean change in temperature; the shaded areas around the lines represent the standard deviation (calculated using n=3). Thermal measurements show that the delivery of the light dose at the 1.3 mW rate limits the heat generated in tumor tissue to less than 1° C. over 2 min irradiation after which the temperature reaches steady state, which is well below thresholds for tissue damage.

These estimates are consistent with the experiments in explanted tumor tissues shown in FIG. 9, which show the penetration of light through about 5 mm thickness. For the selected emission wavelengths, the blood volume fraction of the tissue is important in determining the range of light delivery; the therapeutic volume depends on the type of tumor mass and may be greater for less vascularized tumors. The wireless powering system is capable of achieving these levels of radiant power deep in tissue-like material. In the midfield configuration, the maximum radiant power that can be delivered by the device exceeds 1 mW at a 4 cm depth in water at a transmit power of 2 W. The performance of the system meets the requirements for light delivery to tumors deep in the body and enables illumination of volumes up to ~130 mm3 (assuming a hemisphere volume of radius 4 mm), about 8 times the volume of the device.

Figure 14:
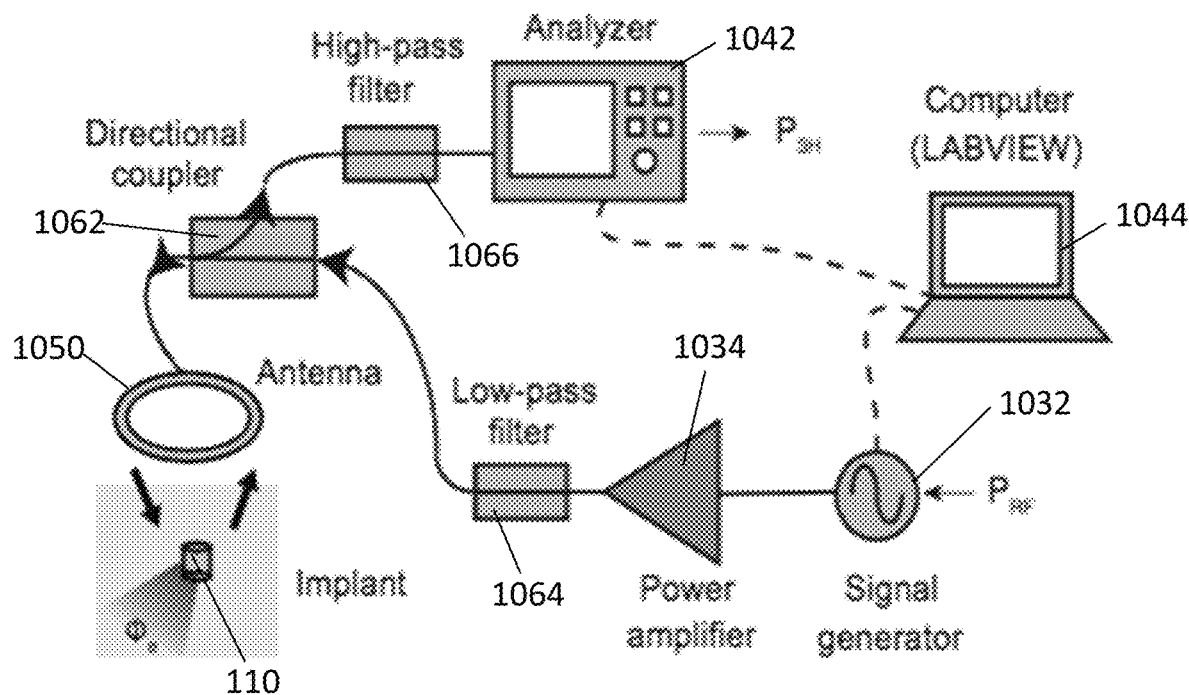
FIG. 14 shows a schematic of the transmitter of the photodynamic therapy system.

FIG. 14 shows a schematic of the transmitter of the photodynamic therapy system. As described above with reference to FIG. 10, the transmitter comprises a powering module, a dosimetry module, an antenna and a coupler. FIG. 14 illustrates the functions of these modules in more detail. As shown in FIG. 14, the power module comprises a signal generator 1032 which generates a radiofrequency signal and a power amplifier 1034 which amplifiers the radiofrequency signal to provide a drive signal for the antenna 1050. A controller 1044 which in this implementation is a computer running LABVIEW software controls the signal generator 1032 to control the power $P_{RF}$ of the radiofrequency signal.

The dosimetry module is formed from a spectrum analyzer 1042 which is coupled to the antenna and configured to measure the power $P_{3H}$ of the third harmonic signal which is backscattered from the implantable illumination device 110 to the antenna 1050. The spectrum analyzer 1042 provides an indication of the power $P_{3H}$ of the third harmonic signal to the controller 1044 which determines the light dose and controls the power of the drive signal.

The coupler which couples the powering module and the dosimetry module to the antenna 1050 is formed from a directional coupler 1062 which provides the output of the power amplifier 1034 to the antenna 1050 and also couples the antenna to the spectrum analyzer 1042. A low-pass filter 1064 is provided between the power amplifier 1034 and the directional coupler 1062 to remove signals with a frequency greater than the radiofrequency drive signal. A high pass-filer 1066 is provided between the directional coupler 1062 and the spectrum analyzer 1042 which prevents the drive signal from the power amplifier 1034 from reaching the spectrum analyzer 1042 to allow the third harmonic signal to be isolated.

Figure 15:
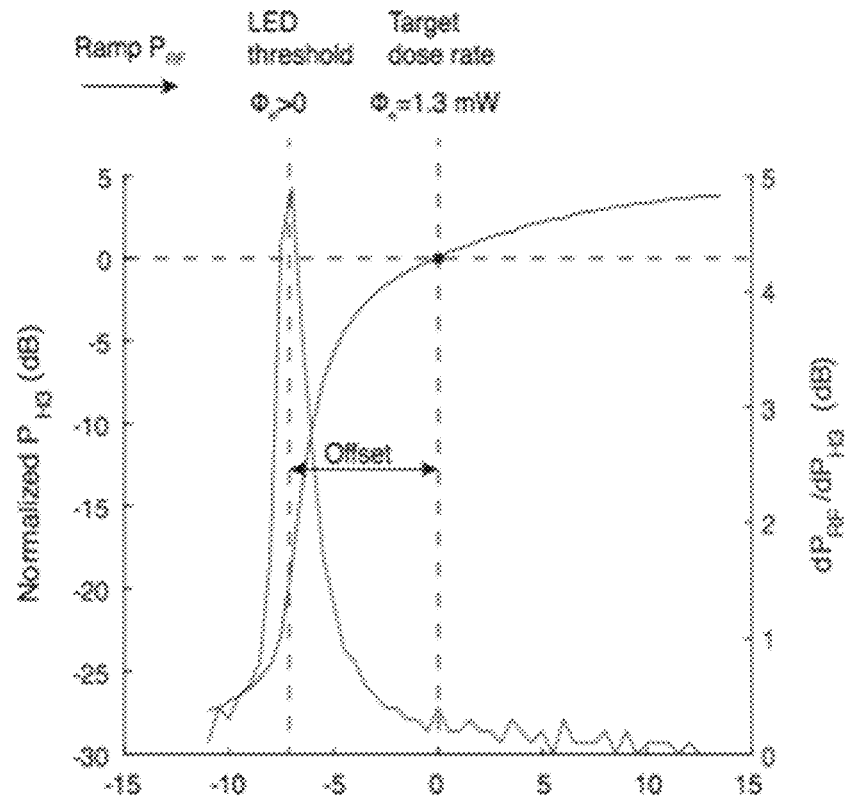
FIG. 15 is a graph showing the power of the third harmonic signal as a function of power level of the radiofrequency drive signal received by the implantable illumination device.

FIG. 15 is a graph showing the power of the third harmonic signal as a function of power level of the radiofrequency drive signal received by the implantable illumination device. FIG. 15 shows the power of the third harmonic signal received by the antenna normalized to the respective power levels at the $\phi_e$=1.3 mW operating point. The derivative $dP_{PH}/dP_{RF}$. As shown in FIG. 15, the harmonic power abruptly increases around LED threshold, from which the target dose rate can be established by a predetermined offset. As the device is powered near activation threshold, the non-linearity of the LEDs results in an abrupt increase in the harmonic signal level, which is detected and used as an absolute reference for establishing the desired light dosing rate. The backscattered harmonic signal also facilitates the placement of the transmitter on the body surface in order to optimize the transfer efficiency and avoid misalignment between transmitter and receiver.

To illustrate that the implantable illumination devices could be powered through thick tissue at depths relevant to human scales, ROS production studies were conducted in an adult pig model.

Figure 16:
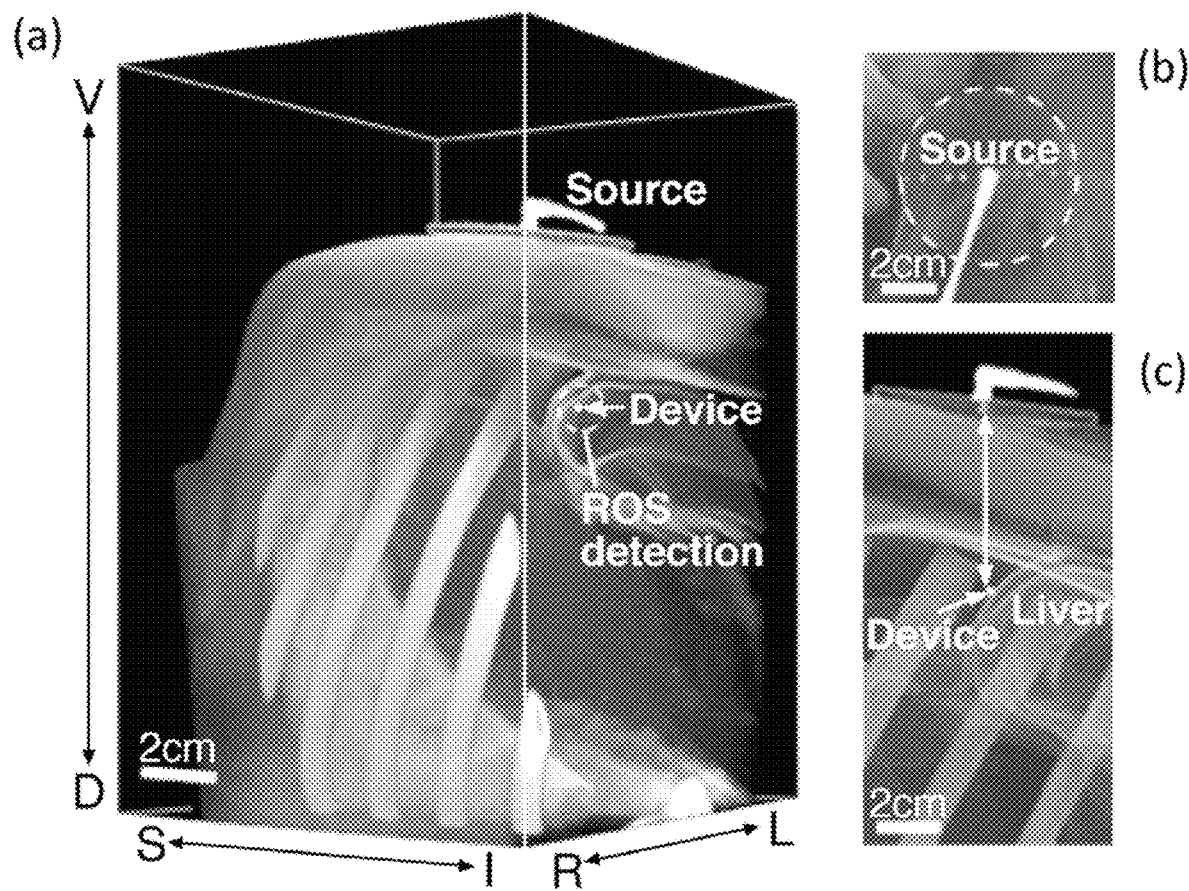
FIGS. 16a to 16c show computed tomography (CT) reconstructions of the radio-frequency transmitter and device implanted an adult pig model.

FIGS. 16a to 16c show computed tomography (CT) reconstructions of the radio-frequency transmitter and device implanted an adult pig model. As shown in FIG. 16a, the device was implanted in the abdomen and ROS detection was carried out in the area surrounding the device. As shown in FIG. 16b, the transmitter (Source) was placed on the skin, and as shown in FIG. 16c, the device was placed 5.1 cm deep, on the liver surface.

Figure 17:
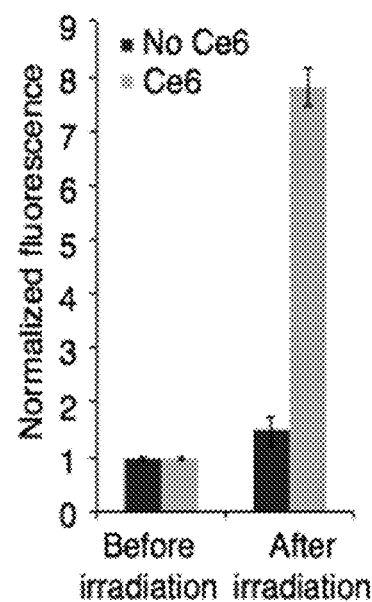
FIG. 17 shows the results for ROS production in Ce6 solution in the region surrounding the device.

FIG. 17 shows the results for ROS production in Ce6 solution in the region surrounding the device. As shown in FIG. 17, wireless light delivery by the device activated Ce6 and caused significant ROS production when powered through the thick intervening tissue. FIG. 17 shows the mean and the error bar represent the standard deviation (n=3 per group). The control (No Ce6) was a control solution with no Ce6 and the test solution was a solution containing 5 μM Ce6.

Using Ce6-incubated murine bladder cancer cells, ROS production was further validated against red laser irradiation, the current clinical standard, in two configurations: (i) cells directly exposed to the radio-frequency/laser source, and (ii) cells placed under thick (3 cm) porcine tissue, simulating light delivery to deep tissue regions.

Figure 18:
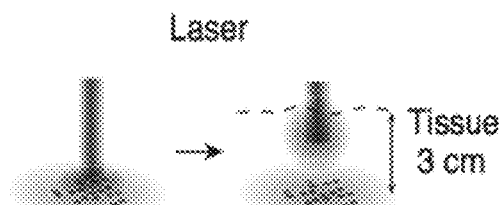
FIGS. 18a to 18d illustrate test configurations for investigating ROS production.

FIGS. 18a to 18d illustrate test configurations for investigating ROS production. FIG. 18a illustrates a test configuration in which laser light is directly incident on the MB49 cells and FIG. 18 illustrates a test configuration in which the laser light travels through 3 cm of tissue. The laser illumination was carried out with the following intensity 37.5 mW/cm$^2$, 4 J/cm$^2$. FIG. 18c illustrates a test configuration in which a wirelessly powered implantable device is powered without intervening tissue. For this configuration near-field (NF) wireless powering was used. FIG. 18d illustrates a test configuration in which a wirelessly powered implantable device is powered without though 3 cm of tissue. For this configuration mid-field (MF) wireless powering was used.

Figure 19:
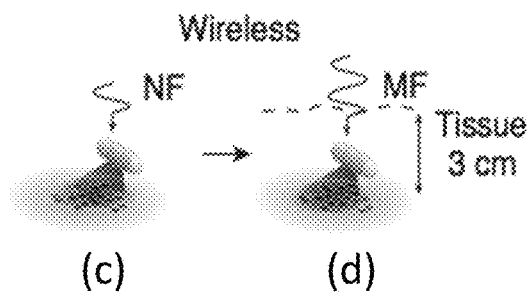
FIG. 19 shows the results showing cell viability for the test configurations shown in FIGS. 18a to 18d.
Figure 19:
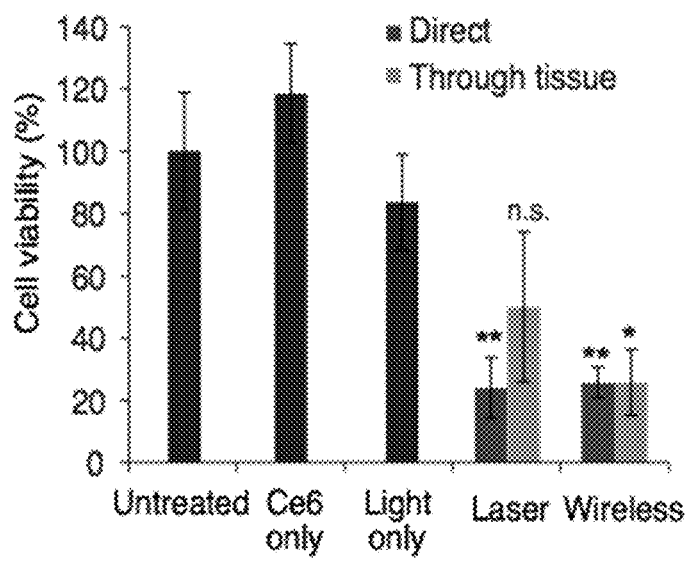

FIG. 19 shows the results showing cell viability for the test configurations shown in FIGS. 18a to 18d. Change in cell viability (MTS assay) following 20 min of irradiation in the above light delivery configurations is shown. The light dosing rate was 1.3 mW throughout. Groups include untreated cells, cells exposed to Ce6 alone, cells exposed to light alone and cells incubated with Ce6 and exposed to light from a laser or the device with or without intervening tissue section. As can be seen from FIG. 19, illumination with the wirelessly powered implantable device resulted in significantly reduced cell viability for both the direct and the through tissue scenarios. Laser illumination was effective at reducing cell viability in the direct scenario but not in the through tissue scenario. Specifically, wireless light delivery resulted in nearly 80% cell kill in both configurations (P=0.0027 direct and P=0.0039 through thick tissue), whereas laser illumination obstructed by thick tissue did not result in a significant difference in cell viability (P=0.178).

Figure 20:
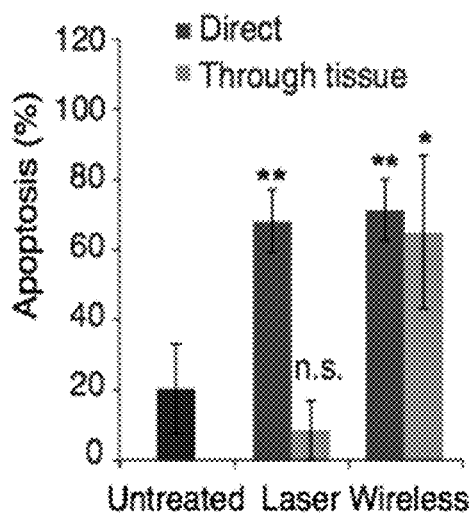
FIG. 20 shows apoptosis for the test configurations shown in FIGS. 18a to 18d.

Cell death could be attributed to apoptosis, a widely accepted mechanism for PDT-mediated cytotoxicity. FIG. 20 shows apoptosis for the test configurations shown in FIGS. 18a to 18d. Apoptosis index (TUNEL assay) including positive and negative controls from the assay are shown. As shown in FIG. 20 there is high apoptosis for both wireless scenarios, but only for the direct laser scenario. In the through tissue laser configuration, the apoptosis is low and comparable to the untreated control scenario.

Figure 21:
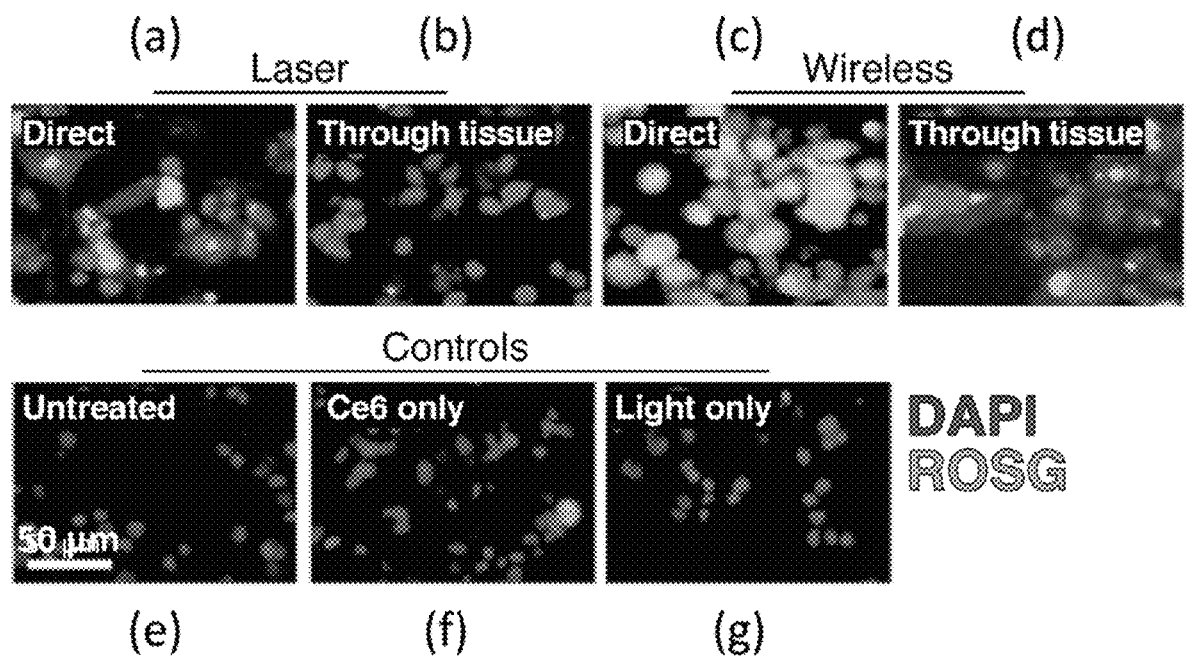
FIGS. 21a to 21g show florescence images of treated cells and control cells.

FIGS. 21a to 21g show florescence images of treated cells and control cells. FIGS. 21a and 21b show cells treated following incubation with Ce6 and illuminated with respectively, the direct laser configuration and, the though tissue laser configuration. FIGS. 21c and 21d show cells treated following incubation with Ce6 and illuminated with respectively, the near field (direct) wireless configuration and, the though tissue (mid field) wireless configuration. FIGS. 21e to 21g show control scenarios. FIG. 21e shows untreated cells. FIG. 21f shows cells subjected to Ce6 only and FIG. 21g shows cells subjected to light only. The results were obtained from a fluorogenic, cell-permeable ROS sensor (Image-iT live Green ROS).

As can be seen from the results described above, wireless illumination with the device resulted in increased signal both in close proximity to the radio-frequency source and through thick tissue. In contrast, laser illumination was effective only under direct irradiation: obstruction of the beam with thick tissue resulted in insignificant ROS-induced fluorescence. Controls consisting of light, radio-frequency field, or Ce6 exposure alone also did not result in significant ROS production. In all cases, significant cell death resulted from oxidative stress. These results demonstrate successful light-based targeting of malignant cells in regions inaccessible by direct laser illumination.

We next demonstrated the efficacy of the light delivery system for cancer PDT in C57 BL/6 mice. The cancer model enables the therapeutic effect of the light dose to be tested in vivo, although the small size of the animals does not reproduce the depth of target region.

Figure 22:
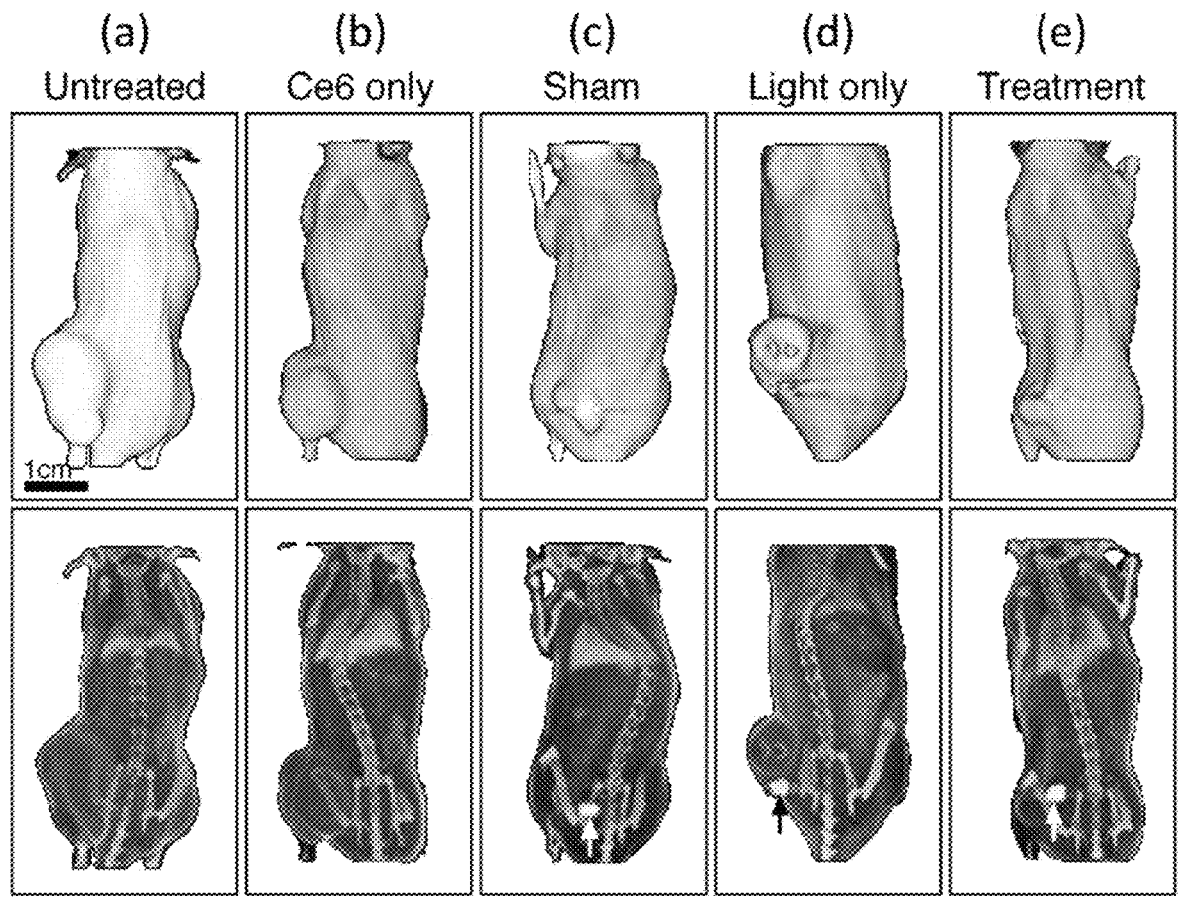
FIGS. 22a to 22e show computed tomography reconstructions of representative mice in five groups
Figure 23:
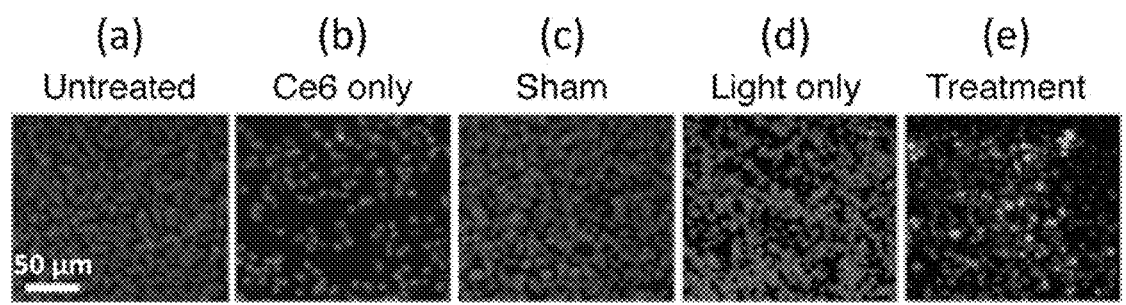
FIGS. 23a to 23e show stained tumor tissue sections corresponding to the test groups shown in FIGS. 22a to 22e

FIGS. 22a to 22e show computed tomography reconstructions of representative mice in five groups. The images were taken 13 days after first treatment. FIG. 22a shows an untreated mouse, FIG. 22b shows a mouse treated with Ce6 only, FIG. 22c shows a mouse with an illumination device implanted at the location indicated by the white arrow, but without activation or treatment with Ce6. FIG. 22d shows a mouse with an illumination device implanted at the location indicated by the white arrow which was activated with an radiofrequency signal, and the mouse was not treated with Ce6. FIG. 22e shows a mouse with an illumination device implanted at the location indicated by the white arrow which was activated with an radiofrequency signal, which was treated with Ce6.

FIGS. 23a to 23e show stained tumor tissue sections from each group described above with reference to FIGS. 22a to 22e. DAPI (dark grey) shows cell nuclei and TUNEL (light grey) staining indicates apoptosis.

Figure 24:
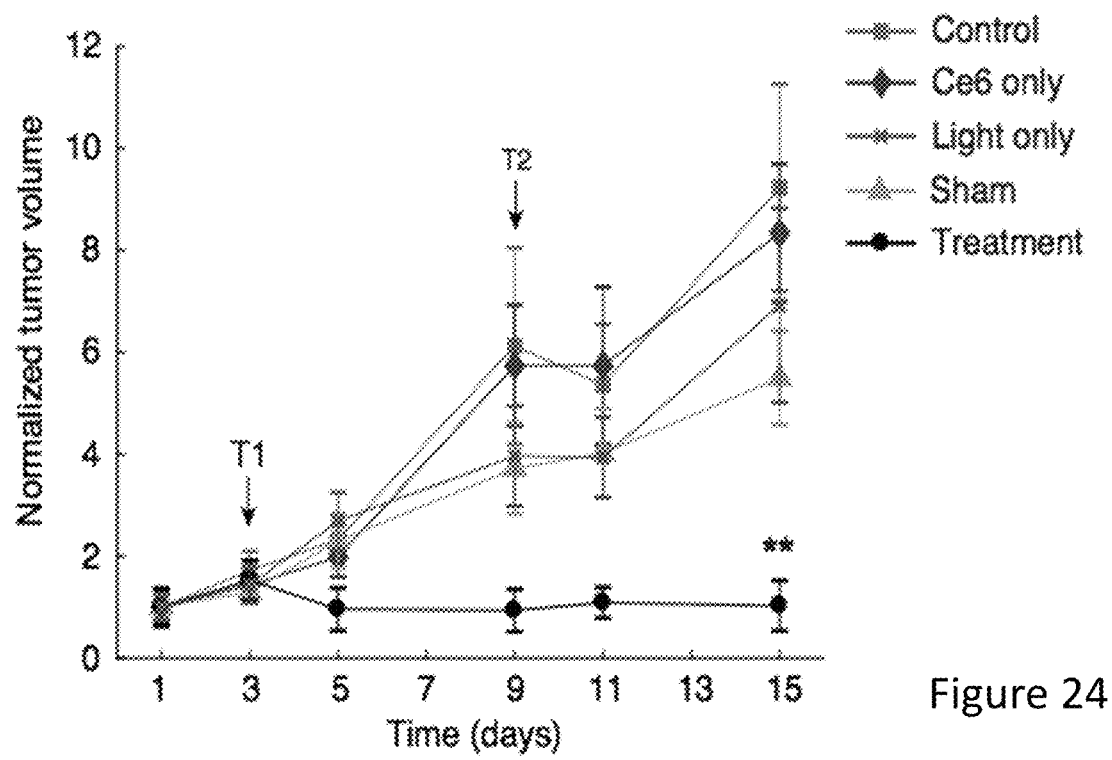
FIG. 24 shows normalized tumor volume as a function of time during a monitoring period.

FIG. 24 shows normalized tumor volume as a function of time during the monitoring period. Treatments were administered on Day 3 (T1) and Day 9 (T2) with a light dose of 1.3 mW over 30 min. Graphs show mean±s.d. (n=5 per group).

Figure 25:
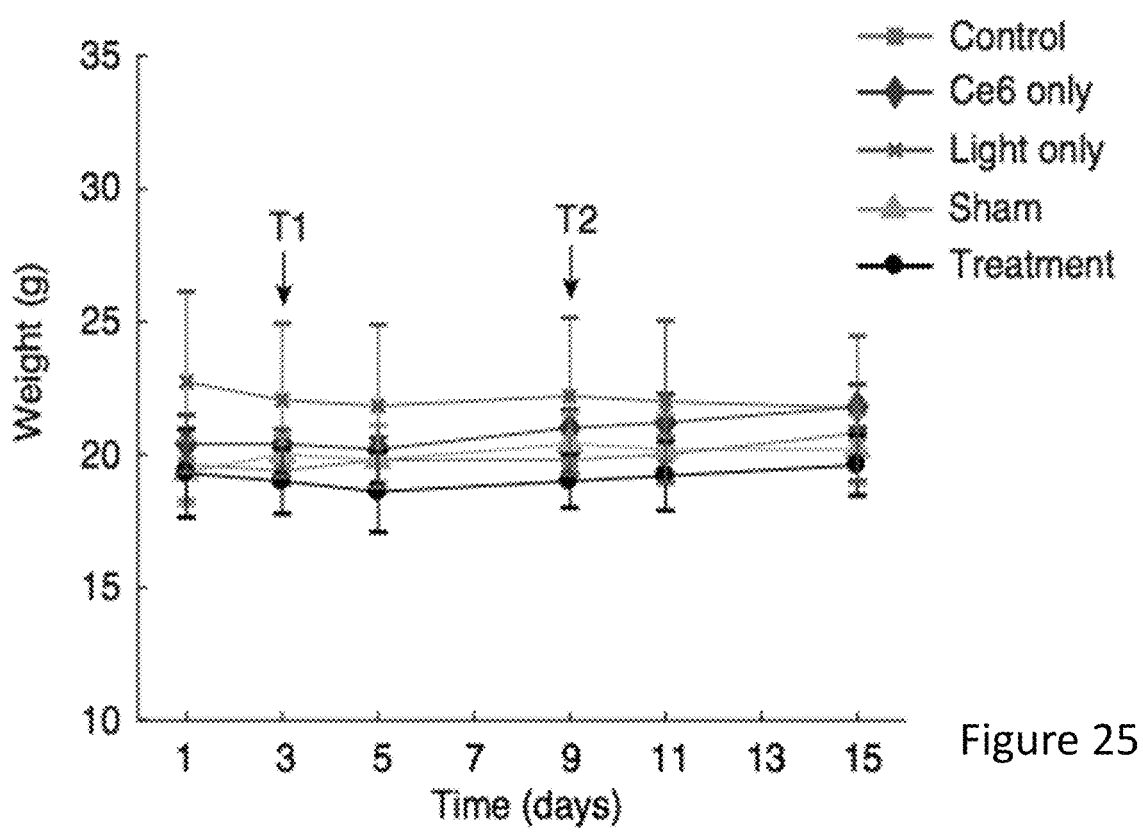
FIG. 25 shows body weight over a treatment period.

FIG. 25 shows body weight over the treatment period. As mentioned above with reference to FIG. 24, were administered on Day 3 (T1) and Day 9 (T2).

The light dose was set to the same level (1.3 mW, 30 min) as used in the in vitro experiments. Devices were implanted in the interstitial space around a solid tumor grown to 4-6 mm diameter from MB49 bladder cancer cells subcutaneously injected into the hind region. After a recovery period, PDT was performed by intratumoral injection of Ce6 followed 4 hours later by wireless delivery of the light dose. Photosensitizers administered intratumorally have been shown to be retained in tumors for several hours, which is sufficient for the duration of the treatment. A second round of treatment was administered 7 days after the first, demonstrating ease of light delivery over long time scales. Control groups were left untreated; received Ce6 injections only, received sham devices only, or given light doses using functional devices without Ce6 injection.

Monitoring of the tumor volume as a function of time revealed suppression, and in some cases complete regression, of tumors in the treatment group compared to control groups. Wireless delivery of light dose alone did not significantly affect tumor growth, indicating that the treatment efficacy was not due to the mild thermal effect of light and/or radio-frequency field exposure. Monitoring of tumor volume ended 13 days after first treatment, beyond which tumors in the majority of the mice from control groups either reached ethical size limits or were ulcerated. Across all groups, mice were otherwise healthy and did not show appreciable weight loss. Resection and histological examination (cryosectioning and TUNEL staining) of tumors revealed a significantly greater population of apoptotic cells in the treatment group compared to control groups, indicating that photodynamic activity is the likely mechanism for tumor destruction. Tumor volumes cleared by PDT at the prescribed light dose are consistent with light transport calculations and measurements.

We compared the therapy to PDT by direct laser illumination, the current clinical standard, by histological examination of the tissue following a single round of treatment.

Figure 26:
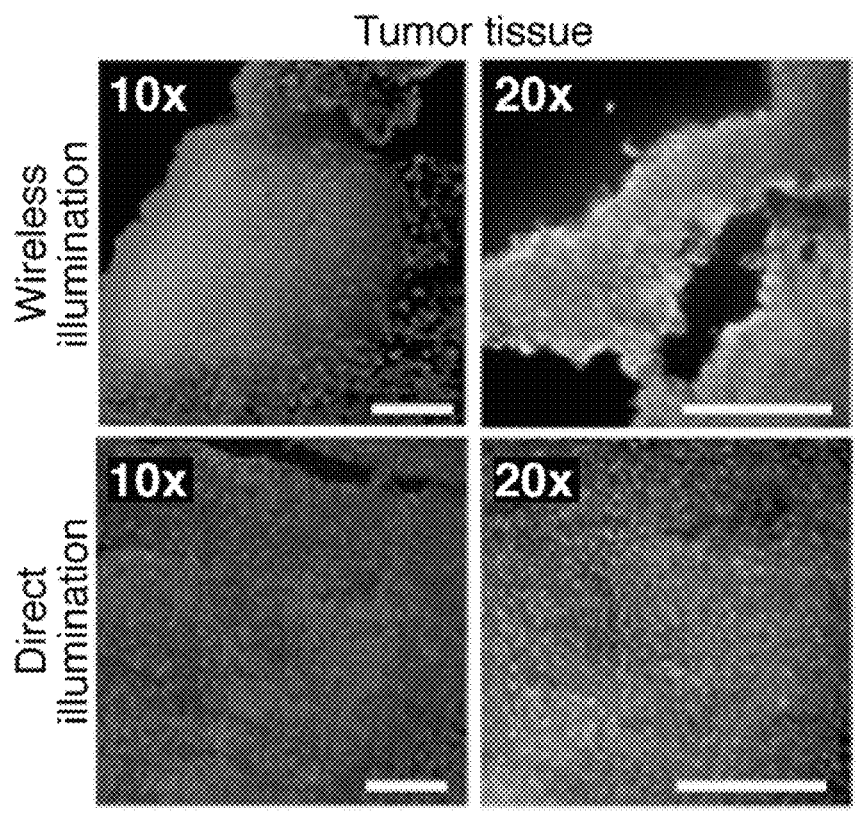
FIG. 26 shows stained sections of tumor tissue following a single round of treatment using either wireless light delivery or laser light delivery.

FIG. 26 shows stained sections of tumor tissue following a single round of treatment using either wireless light delivery (wireless illumination) or laser light (660 nm) delivery (direct illumination).

Figure 27:
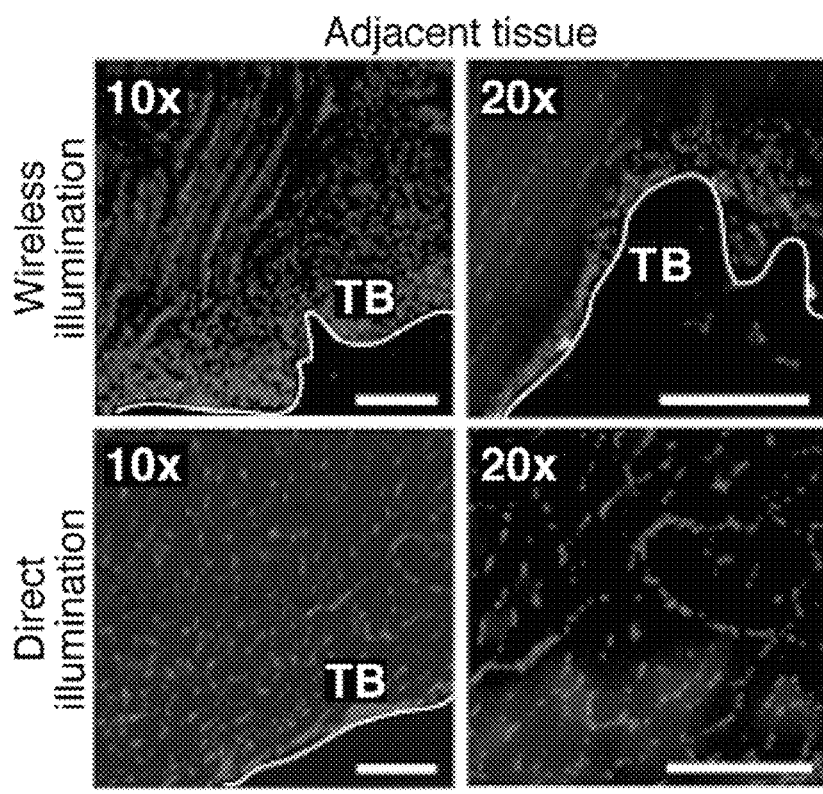
FIG. 27 shows stained sections of healthy tissues adjacent to the tumor.

FIG. 27 shows stained sections of healthy tissues adjacent to the tumor. The white lines labelled "T.B." indicates a tissue boundary.

Tumor-bearing mice were injected intratumorally with Ce6 and administered either the prior light dose using the wireless device or using a red laser (660 nm) collimated to a 5-mm diameter spot. In both cases, explanted tumor tissues showed comparable apoptosis, but tissues sampled from regions adjacent to the tumor did not show significant damage as assessed by TUNEL staining. Thermal measurements show that radio-frequency field exposure induces less than 2° C. increase in skin temperature after 4 min of operation and was less than laser illumination. These results suggest that PDT by wireless light delivery does not result in increased damage to healthy tissues compared to current clinical standards. . . .

The system can be adapted for use with other photosensitizers. As an example, direct LED illumination of zinc phthalocyanine (ZnPc) and protoporphyrin IX (PpIX), two other clinically used photosensitizers with an absorption peak near 660 nm, also resulted in comparable levels of ROS in vitro.

Figure 28:
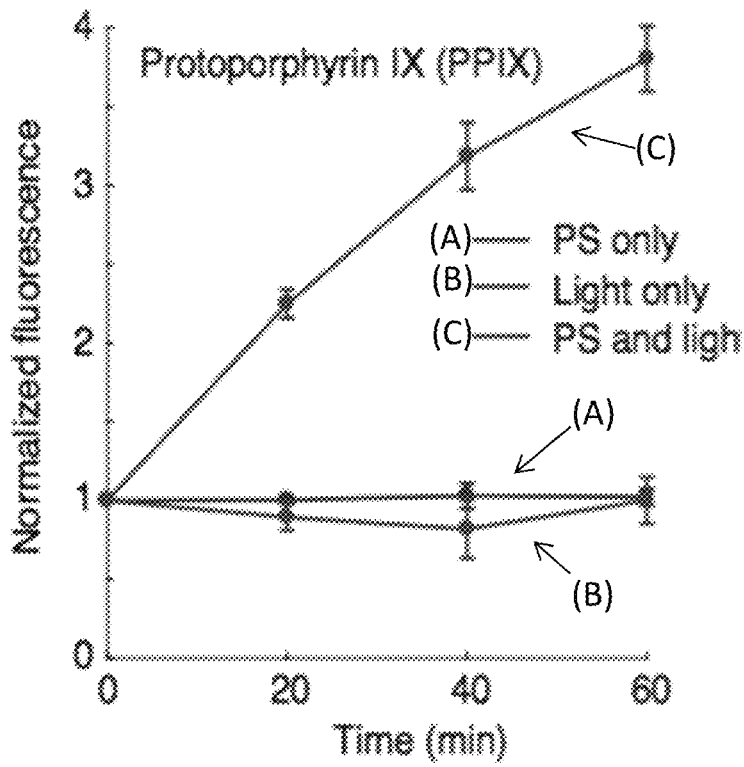
FIG. 28 shows normalized fluorescence results for protoporphyrin IX as a photosensitizer.

FIG. 28 shows normalized fluorescence results for protoporphyrin IX as a photosensitizer.

Figure 29:
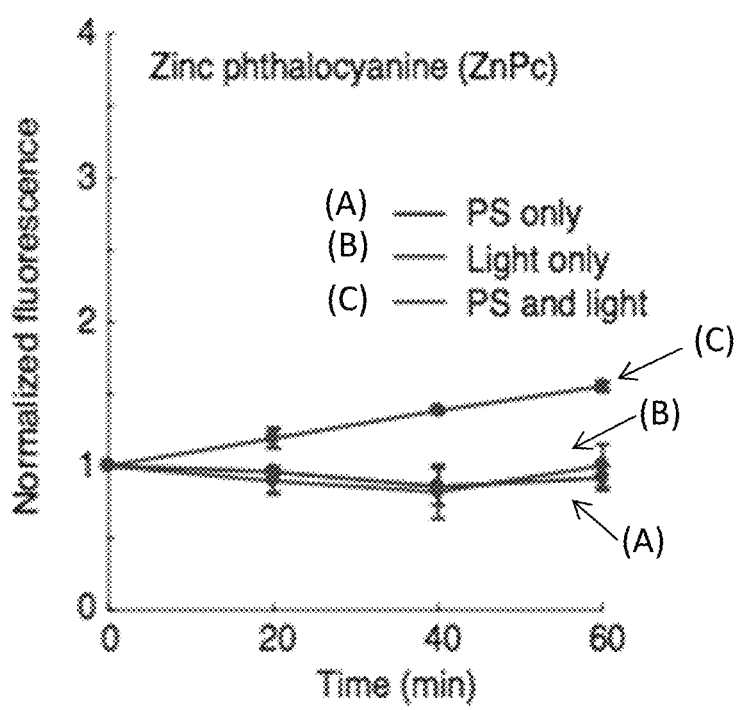
FIG. 29 shows normalized fluorescence results for zinc phthalocyanine as a photosensitizer.

FIG. 29 shows normalized fluorescence results for zinc phthalocyanine as a photosensitizer.

The selection of LEDs with emission wavelengths tuned to match the absorption peaks can further enhance PDT.

Figure 30:
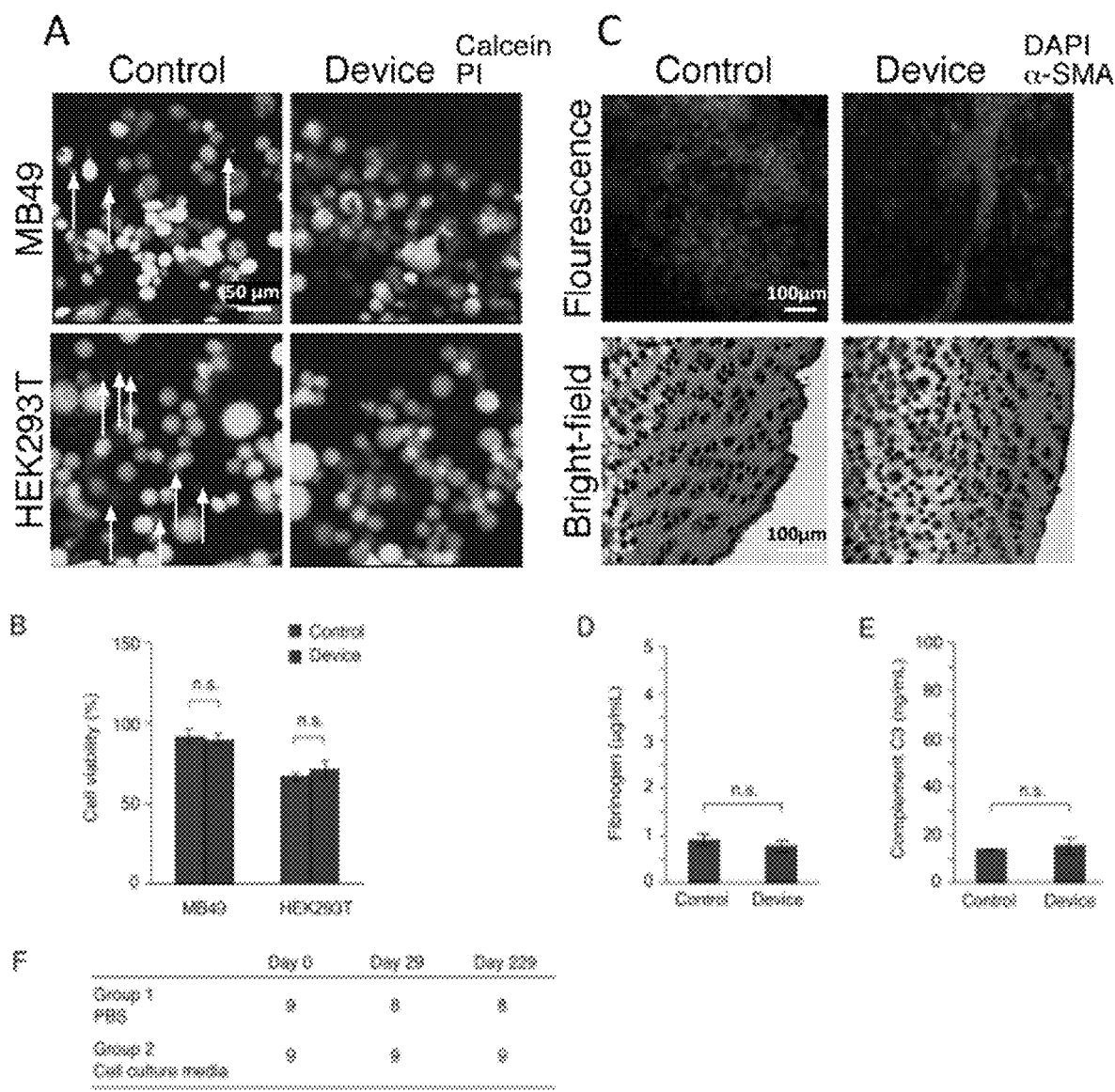
FIGS. 30A to 30F illustrate results demonstrating device biosafety.

FIGS. 30A to 30F illustrate results demonstrating device biosafety. FIG. 30A shows confocal fluorescence microscopy images of MB49 (cancer) and HEK293T (non-cancer) cells grown on the device for 3 days. The grey fluorescence (calcein ex/em 488/520 nm) indicates live cells and the white arrows (PI, ex/em 488/635 nm) indicate dead cells. Control cells were incubated without the device. FIG. 30B shows viability analysis of MB49 and HEK293T cells. FIG. 30C shows Histological analyses of tissues around device implanted for 3 weeks. Tissues were stained for alpha smooth muscle actin (α-SMA) in addition to H&E staining (scale bar 100 μm). Control tissues were obtained from non-implanted mice. FIGS. 30D and 30E illustrate Fibrinogen and Complement C3 concentration in plasma from implanted (device) and non-implanted mice (control) measured by ELISA. FIG. 30F shows the number of functional devices following submersion in phosphate-buffered solution (PBS) and cell culture media at 37° C. Graphs show mean±s.d. (n=3 per group).

Potential clinical targets of our wireless PDT approach include hepatocellular carcinomas (liver tumors) or glioblastomas (brain tumors), where PDT currently provides promising outcomes compared to conventional treatment, but has been hindered by the inaccessibility of the target region to light. An example of a wireless implantable illumination device for treatment of brain tumors is described below.

Figure 31:
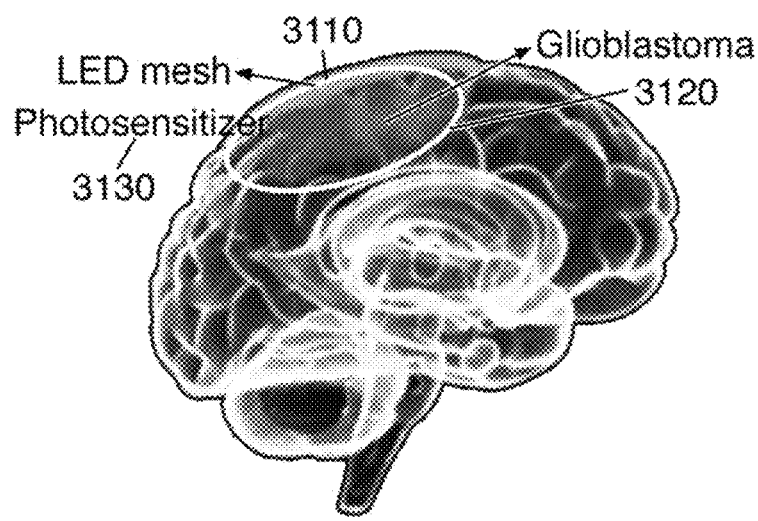
FIG. 31 shows an implantable illumination device for treatment of a brain tumor.

FIG. 31 shows an implantable illumination device for treatment of a brain tumor. As shown in FIG. 31, the wireless implantable illumination device 3110 is a thin, flexible device, which comprises mesh of light emitting diode (LEDs). This allows the wireless implantable illumination device 3110 to be implanted in the narrow confines beneath the skull of the subject. The wireless implantable illumination device 3110 is implanted close to the glioblastoma 3120 and as described above, light emitted from the wireless implantable illumination device 3110 activates a photosensitizer 3130 in the vicinity of the glioblastoma 3120.

Figure 32:
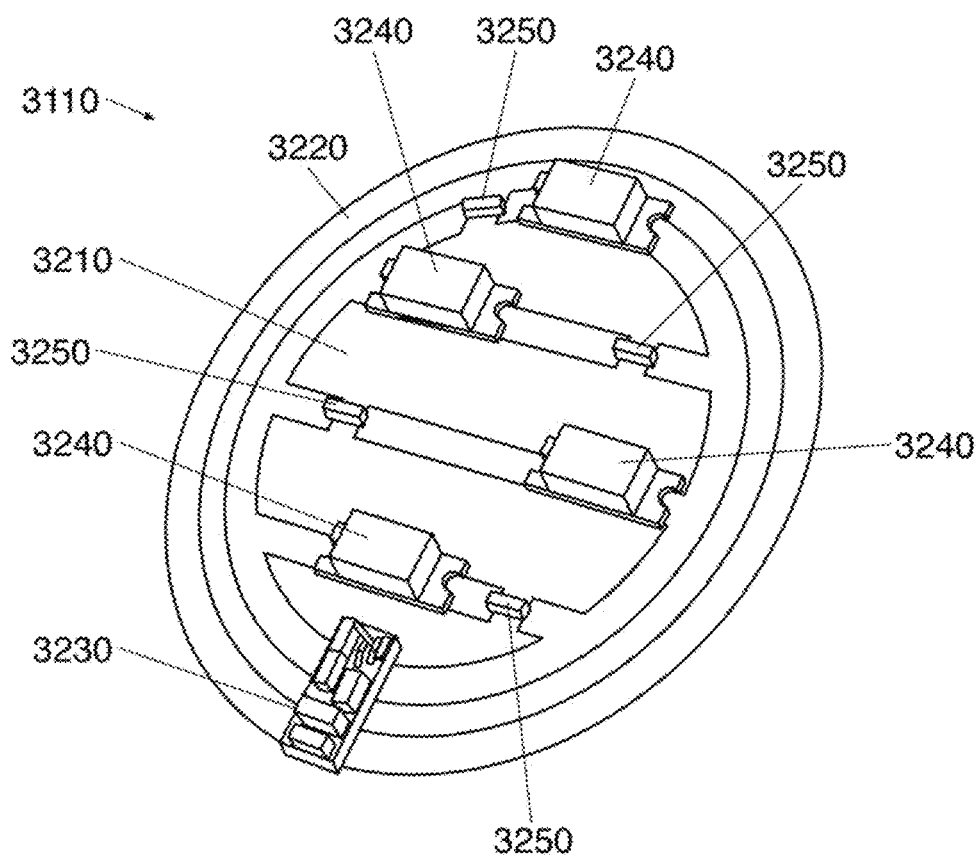
FIG. 32 shows the implantable illumination device for treatment of a brain tumor.

FIG. 32 shows the implantable illumination device shown in FIG. 31. As shown in FIG. 32, the implantable illumination device 3110 is formed from on a substrate 3210. The substrate 3210 is formed from a flexible material such as polyimide. The substrate 3210 is circular and a receiver antenna 3220 is formed as circular loop of copper on the substrate 3210 around the edge. A rectifier 3230 which comprises a plurality of diodes and capacitors is coupled to two ends of the receiver antenna 3220. It is noted that a gap is formed between the two ends of the circular loop of the receiver antenna 3220. The receiver antenna 3220 is connected across the alternating current (AC) input of the rectifier 3230. A plurality of light emitting diodes (LEDs) 3240 are connected in parallel across the direct current (DC) output of the rectifier 3230. A resistor 3250 is connected in series with each of the LEDs 3240.

The implantable illumination device 3110 shown in FIG. 32 may be encapsulated in an encapsulation material in a similar manner to the device described above with reference to FIGS. 3 to 5. The arrangement of LEDs may be varied, for example pairs of red and violet LEDs may be arranged on the device or other combinations of LEDs may be arranged on the device.

The implantable illumination device 3110 shown in FIG. 32 may be used with a transmitter of a wireless power signal such as that described above with reference to FIG. 10.

Depending on the absorption spectrum of the photosensitizer used and the size of the tumor, the devices can be customized to emit a suitable light wavelength. The photosensitizer Ce6 (chlorin e6) has a strong absorption peak at 405 nm and a weaker one at 660 nm. Using LED meshes that emit either 405 nm or 660 nm light, the activation of the photosensitizer and generation of reactive oxygen species (ROS) was demonstrated. This is shown in FIGS. 33A and 33B.

Figure 33A:
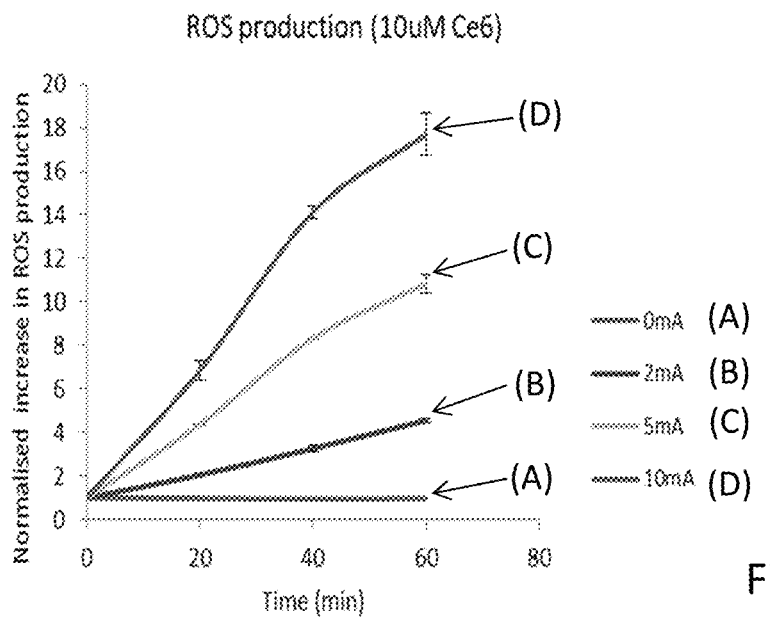
FIGS. 33A and 33B are graphs showing production of reactive oxygen species (ROS) by Ce6 when illuminated using a wireless illumination device emitting red (660 nm) light, and UV/violet (405 nm) light respectively.

FIG. 33A is a graph showing production of reactive oxygen species (ROS) by Ce6 when illuminated using a wireless illumination device emitting red (660 nm) light. FIG. 33B is a graph showing production of reactive oxygen species (ROS) by Ce6 when illuminated using a wireless illumination device emitting UV/violet (405 nm) light.

Figure 33B:
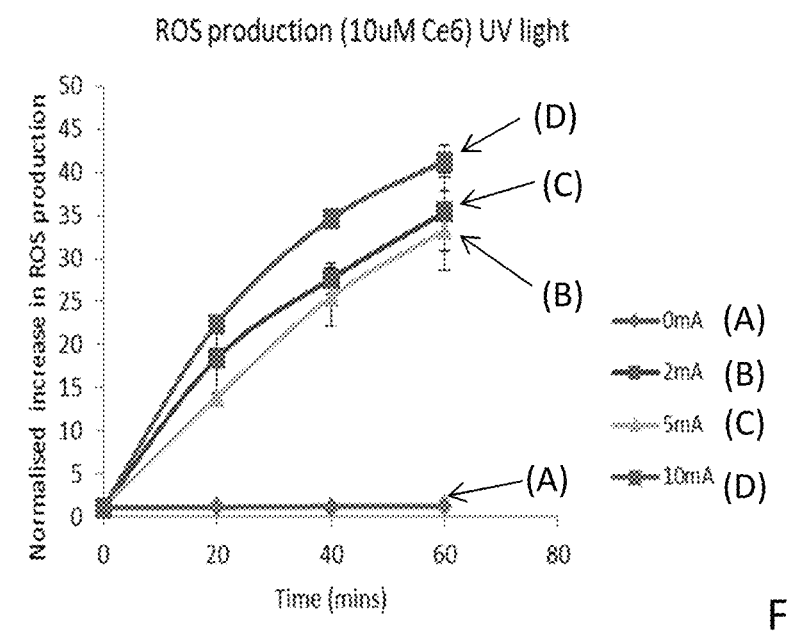

From a comparison of FIGS. 33A and 33B, it can be seen that ROS yield is higher when UV/violet light is used. The 405 nm light was more effective than the 660 nm light in ROS generation owing to the stronger absorption peak of Ce6 at the 405 nm wavelength.

Figure 34:
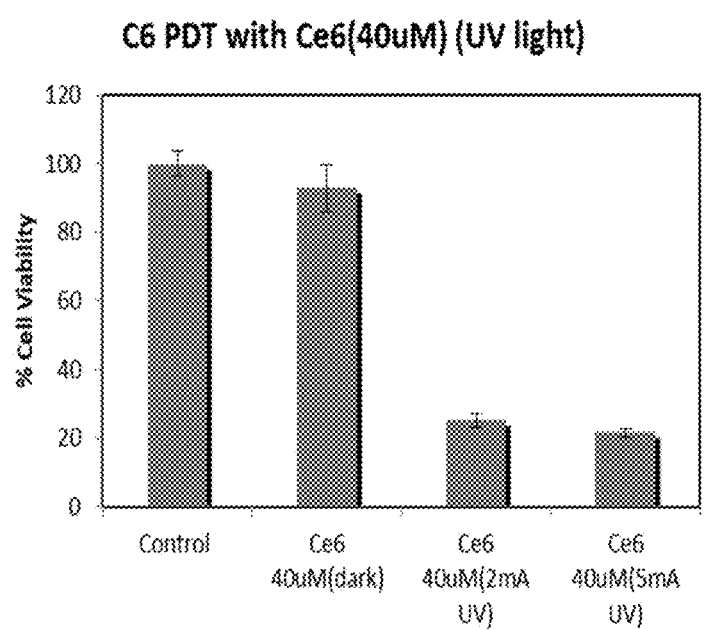
FIG. 34 shows the cell kill in C6 rat glioma due to UV light triggered photodynamic therapy using the photosensitizer Ce6.

FIG. 34 shows the cell kill in C6 rat glioma due to UV light triggered photodynamic therapy (PDT) using the photosensitizer Ce6. From FIG. 34, it can be seen that PDT triggered by UV/violet light emitting devices resulted in about 80% cell death of c6 rat glioma cells in vitro.

In the visible range (400-700 nm) of the spectrum, the maximum depth penetration through tissue is less than 5 mm, even when using red light. For shorter wavelengths such as UV light, this reduces to about 1 mm. To treat larger tumors using PDT, longer wavelengths such as those in the near infrared range (NIR) are needed. These wavelengths can be used in conjunction with NIR to visible light transducers like upconversion nanoparticles (UCNP) to extend the range of PDT.

Figure 35:
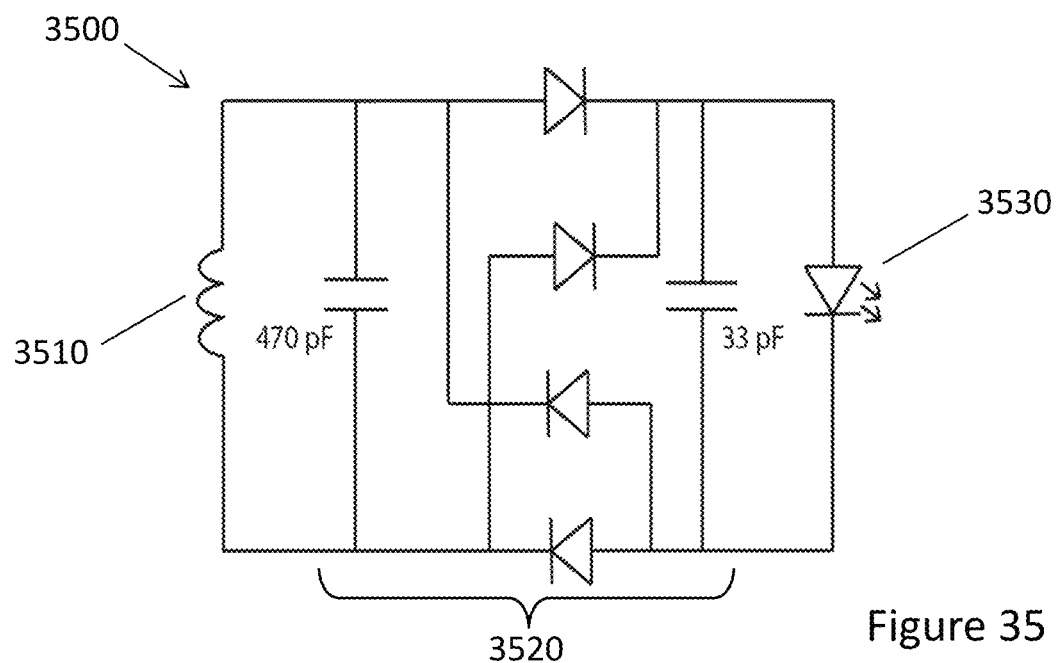
FIG. 35 shows a schematic circuit diagram of a near infra-red (NIR) light emitting implantable illumination device.

FIG. 35 shows a schematic circuit diagram of a near infra-red (NIR) light emitting implantable illumination device. The implantable illumination device 3500 comprises a receiver antenna 3510 which is connected across the AC input of a rectifier circuit 3520. A NIR LED 3530 is connected across the DC output of the rectifier circuit 3520. The NIR LED 3530 emits light having a wavelength of 980 nm. The rectifier circuit 3520 comprises four diodes and two capacitors. Additional NIR LEDs may be connected in parallel with the NIR LED 3530.

Figure 36:
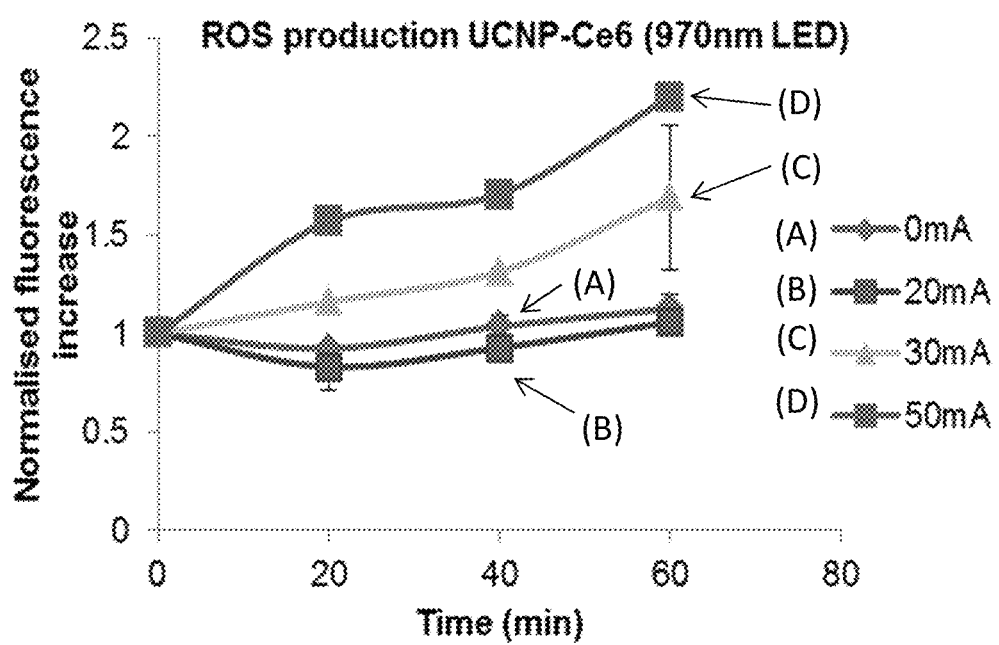
FIG. 36 shows reactive oxygen species production triggered by up-converted blue light from up-conversion nanoparticles illuminated with a NIR light emitting device.

FIG. 36 shows reactive oxygen species (ROS) production triggered by up-converted blue and red light emitted from up-conversion nanoparticles with an $NaYF_4$ (sodium yttrium fluoride) matrix doped with $Yb^+$(Ytterbium)/$Er^{3+}$(Erbium) ions, when illuminated with a NIR light emitting device. As shown in FIG. 36 for currents of 30 mA and above a significant increase in ROS production occurs.

We have demonstrated a wireless implantable photonic device that achieves therapeutic light delivery for cancer PDT. The operation of the device deep in the body is enabled by a radio-frequency system for wireless powering and monitoring of the light dose. As proof of concept, we wirelessly activated photosensitizers in situ in a porcine model of tissue and suppressed tumor activity in vivo in a murine cancer model by delivering light doses for PDT. The versatility of light delivery enabled by this approach overcomes the depth limitation of conventional PDT and extends its spatiotemporal precision to regions not directly accessible to light.

Potential clinical targets for which our approach could provide advantages include hepatocellular carcinomas or glioblastomas, where PDT currently provides promising outcomes compared to conventional treatment, but has been hindered by the inaccessibility of the target region to light. The versatility of light delivery allows light doses to be delivered over long time scales in a programmable and repeatable manner, and could potentially enable the therapies to be tailored in real-time.

Whilst the foregoing description has described exemplary embodiments, it will be understood by those skilled in the art that many variations of the embodiments can be made within the scope and spirit of the present invention.

The invention claimed is:

1. A photodynamic therapy system comprising:
    an implantable illumination device comprising a light source configured to emit light having a spectrum which overlaps with an absorption peak of an absorption target and a receiver antenna coupled to the light source and configured to extract power from a radiofrequency power signal incident on the implantable illumination device; and
    a transmitter comprising an antenna, a powering module configured to generate a drive signal which causes the antenna to generate the radiofrequency power signal, a dosimetry module coupled to the antenna and configured to measure a power, at the antenna, of a third harmonic of the radiofrequency power signal backscattered from the implantable illumination device, and a controller configured to determine, based on the power, at the antenna, of the third harmonic of the radiofrequency power signal backscattered from the implantable illumination device, an indication of the power extracted by the implantable illumination device from the radiofrequency power signal incident on the implantable illumination device, determine a light dose emitted by the light source based on the indication of the power extracted by the implantable illumination device, and control the drive signal to control a power of the radiofrequency power signal and thereby control the light dose.

2. A photodynamic therapy system according to claim 1, wherein the light source comprises a first light emitting device configured to emit light having a first wavelength and a second light emitting device configured to emit light having a second wavelength different from the first wavelength.

3. A photodynamic therapy system according to claim 1, wherein the implantable illumination device comprises a planar substrate and wherein the light source comprises a plurality of light emitting devices arranged on the planar substrate.

4. A photodynamic therapy system according to claim 1, wherein the receiver antenna is configured to provide a resonance for a range of frequencies including the radiofrequency power signal.

5. A photodynamic therapy system according to claim 1, wherein the implantable illumination device is encapsulated in an encapsulation material.

6. A photodynamic therapy system according to claim 1, wherein the implantable illumination device comprises a regulator circuit configured to reduce variations emitted light intensity from the light source due to changes in power extracted by the implantable illumination device.

7. A photodynamic therapy system comprising:
an implantable illumination device comprising a light source;
a transmitter comprising an antenna, a powering module configured to generate a drive signal which causes the antenna to generate a radiofrequency power signal to wirelessly provide power to the implantable illumination device, and a dosimetry module coupled to the antenna and configured to measure a power, at the antenna, of a third harmonic of the radiofrequency signal backscattered from the implantable illumination device, and a controller configured to determine, based on the power of the third harmonic of the radiofrequency power signal backscattered from the implantable illumination device, an indication of the power extracted by the implantable illumination device from the radiofrequency power signal incident on the implantable illumination device, determine a light dose emitted by the light source based on the indication of the power extracted by the implantable illumination device, and control the drive signal to control a power of the radiofrequency power signal and thereby control the light dose.

8. A transmitter for a photodynamic therapy system according to claim 7, further comprising a controller configured to modify the drive signal to spatially focus the radiofrequency power signal on the implantable illumination device.

* * * * *